US009982013B2

(12) United States Patent
Davis et al.

(10) Patent No.: US 9,982,013 B2
(45) Date of Patent: May 29, 2018

(54) READILY ISOLATED BISPECIFIC ANTIBODIES WITH NATIVE IMMUNOGLOBULIN FORMAT

(71) Applicant: Regeneron Pharmaceuticals, Inc., Tarrytown, NY (US)

(72) Inventors: Samuel Davis, New York, NY (US); Eric Smith, New York, NY (US); Douglas MacDonald, New York, NY (US); Kara Louise Olson, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 269 days.

(21) Appl. No.: 15/058,026

(22) Filed: Mar. 1, 2016

(65) Prior Publication Data

US 2016/0251395 A1    Sep. 1, 2016

Related U.S. Application Data

(62) Division of application No. 14/034,906, filed on Sep. 24, 2013, now Pat. No. 9,309,326, which is a division of application No. 12/823,838, filed on Jun. 25, 2010, now Pat. No. 8,586,713.

(60) Provisional application No. 61/220,687, filed on Jun. 26, 2009.

(51) Int. Cl.
| | |
|---|---|
| G01N 33/543 | (2006.01) |
| C07K 1/22 | (2006.01) |
| C07K 16/28 | (2006.01) |
| C07K 16/24 | (2006.01) |
| C07K 16/46 | (2006.01) |
| A61K 39/00 | (2006.01) |

(52) U.S. Cl.
CPC .............. *C07K 1/22* (2013.01); *C07K 16/247* (2013.01); *C07K 16/248* (2013.01); *C07K 16/2809* (2013.01); *C07K 16/2866* (2013.01); *C07K 16/2887* (2013.01); *C07K 16/468* (2013.01); *A61K 2039/505* (2013.01); *C07K 2317/21* (2013.01); *C07K 2317/31* (2013.01); *C07K 2317/52* (2013.01); *C07K 2317/526* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,807,706 A | 9/1998 | Carter et al. |
| 5,945,311 A | 8/1999 | Lindhofer et al. |
| 5,985,276 A | 8/1999 | Lindhofer et al. |
| 6,165,745 A * | 12/2000 | Ward ............... C07K 14/70503 435/252.3 |
| 6,551,592 B2 | 4/2003 | Lindhofer et al. |
| 6,994,853 B1 | 2/2006 | Lindhofer et al. |
| 7,018,632 B2 | 3/2006 | Lindhofer et al. |
| 7,169,903 B2 | 1/2007 | Schuman et al. |
| 7,183,076 B2 | 2/2007 | Arathoon et al. |
| 7,220,356 B2 | 5/2007 | Thommes et al. |
| 7,262,028 B2 | 8/2007 | Van Berkel et al. |
| 8,062,640 B2 | 11/2011 | Sleeman et al. |
| 8,592,562 B2 | 11/2013 | Kannan et al. |
| 9,145,588 B2 | 9/2015 | Throsby et al. |
| 2003/0224000 A1 | 12/2003 | Kokai-Kun et al. |
| 2007/0148165 A1 | 6/2007 | Shitara et al. |
| 2007/0196363 A1 | 8/2007 | Arathoon et al. |
| 2009/0263392 A1 | 10/2009 | Igawa et al. |
| 2014/0248664 A1 | 9/2014 | Davis et al. |

FOREIGN PATENT DOCUMENTS

| | | |
|---|---|---|
| GB | 2197322 B | 5/1988 |
| GB | 2197323 B | 5/1988 |
| WO | 2004/009618 A2 | 1/2004 |

OTHER PUBLICATIONS

International Search Report and Written Opinion dated Oct. 6, 2010 with respect to PCT/US2010/040028.
Deisenhofer, J. (1981) "Crystallographic Refinement and Atomic Models of a Human Fc Fragment and its Complex With Fragment B of Protein A from *Staphylococcus aureus* at 2.9- and 2.8-AA Resolution," Biochemistry, 20(9):2361-2370.
Duhamel, et al. (1979) "Ph Gradient Elution of Human Immuno Globulin G-1 Immuno Globulin G-2 and Immuno Globulin G-4 From Protein A Sepharose," Journal of Immunological, 31(3-4):211-217.
Ibrahim, et al. (1993) "Immunoglobulin Binding Specificities of the Homology Regions (Domains) of Protein A," Scandinavian Journal of Immunology 38(4):368-374.
Jendeberg, et al. (1997) "Engineering of Fc1 and Fc3 From Human Immunoglobulin G to Analyse Subclass Specificity for Staphylococcal Protein A," Journal of Immunological Methods, 201(1):25-34.
Lindhofer, et al. (1995) "Preferential Species-Restricted Heavy/Light Chain Pairing in Rat/Mouse Quadromas. Implications for Single-Step Purification of Bispecific Antibodies," Journal of Immunobiology, 155(1):219-225.

(Continued)

*Primary Examiner* — Laura B Goddard
*Assistant Examiner* — Meera Natarajan
(74) *Attorney, Agent, or Firm* — FisherBroylers, LLP; Rita S. Wu; Mary Johnson

(57) ABSTRACT

A bispecific antibody format providing ease of isolation is provided, comprising immunoglobulin heavy chain variable domains that are differentially modified in the CH3 domain, wherein the differential modifications are non-immunogenic or substantially non-immunogenic with respect to the CH3 modifications, and at least one of the modifications results in a differential affinity for the bispecific antibody for an affinity reagent such as Protein A, and the bispecific antibody is isolable from a disrupted cell, from medium, or from a mixture of antibodies based on its affinity for Protein A.

22 Claims, 11 Drawing Sheets

(56) References Cited

OTHER PUBLICATIONS

Lindmark, et al. (1983) "Binding of Immunoglobulins to Protein A and Immunoglobulin Levels in Mammalian Sera" of Immunological Methods, 62(1):1-13.

Nagoaka and Akaike (2003) "Single Amino Acid Substitution in the Mouse IgG1 Fe Region Induces Drastic Enhancement of the Affinity to Protein A," Protein Engineering, 16(4): 243-245.

Ridgway, et al. (1996) "'Knobs-into-holes' Engineering of Antibody CH3 Domains for Heavy Chain Heterodimerization," Protein Engineering, 9(7): 617-621.

Roben, et al. (1995) "VH3 Family Antibodies Bind Domain D of Staphylococcal Protein A," Journal of Immunology 154(12):6437-6445.

Starovasnik, et al. (1999) "Antibody Variable Region Binding by Staphylococcal Protein A: Thermodynamic Analysis and Location of the Fv Binding Site on E-domain," 1423-1431.

Van Loghme, et al. (1982) "Staphylococcal Protein A and Human IgG Subclasses and Allotypes," Scandinavian Journal of Immunology, 15(3):275-278.

Third party observations filed on Aug. 10, 2012 by Maclean, Martin R in the corresponding European Patent Application (EP1 0726775.9).

\* cited by examiner

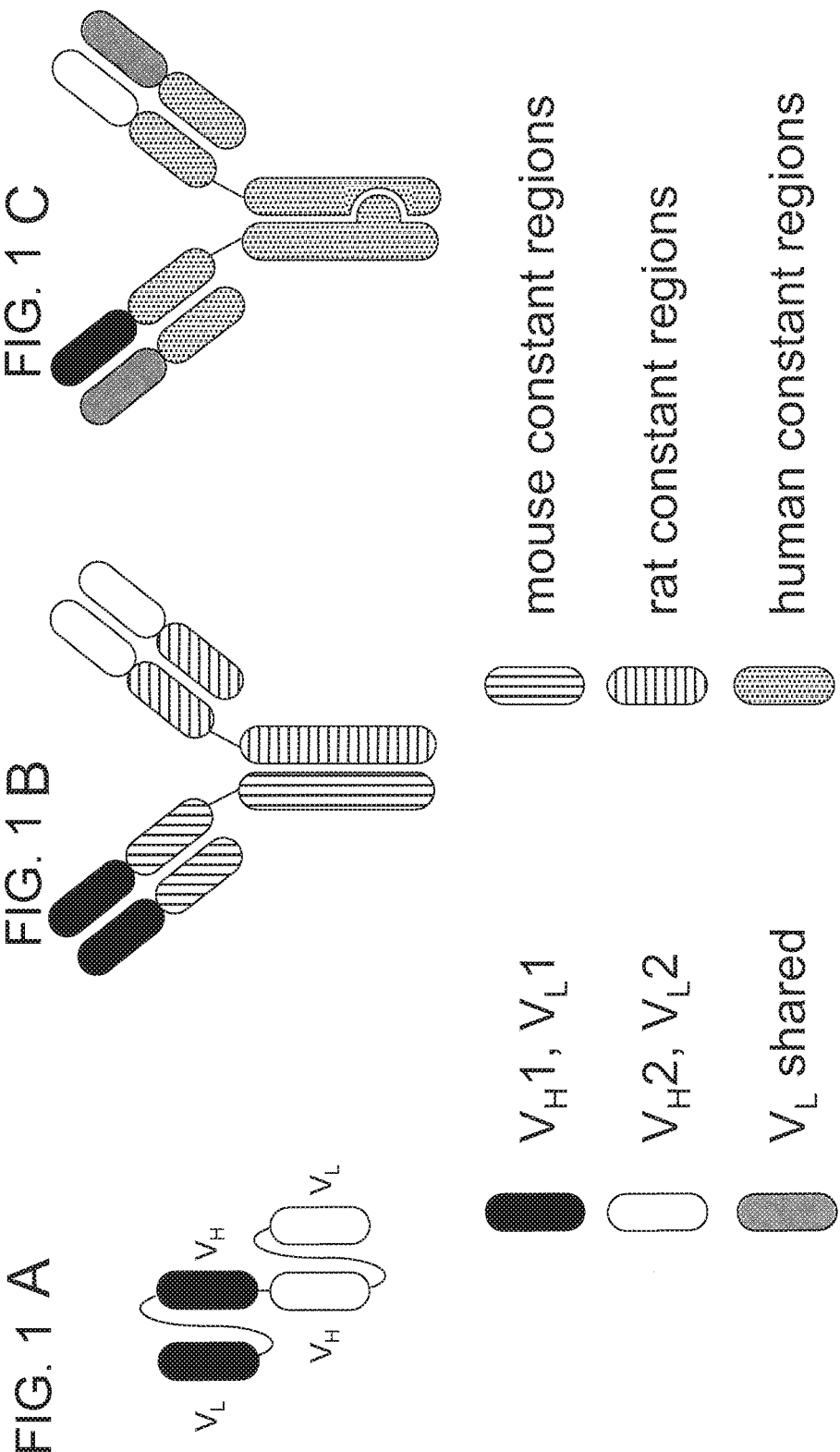

```
IgG1 252 MISRTPEVTCVVVDVSHEDPEVK FN WYVDGVEVHNAKTKPREEQYNST Y  300
IgG3 252 MISRTPEVTCVVVDVSHEDPEV QK  WYVDGVEVHNAKTKPREEQYNST F  300

IgG1 301 RVVSVLTVLHQDWLNGKEYKCKVSNKALPAPIEKTISK A KGQPREPQV Y  349
IgG3 301 RVVSVLTVLHQDWLNGKEYKCKVSNKALPAPIEKTISK T KGQPREPQV Y  349

IgG1 350 TLPPSREEMTKNQVSLTCLVKGFYPSDIAVEWES N GQPENNY K TTPP V L 398
IgG3 350 TLPPSREEMTKNQVSLTCLVKGFYPSDIAVEWES S GQPENNY N TTPP M L 398

IgG1 399 DSDGSFFLYSKLTVDKSRWQQGNVFSCSVMHEALHN HYTQKSLSLSPGK 447
IgG3 399 DSDGSFFLYSKLTVDKSRWQQGNIFSCSVMHEALHN RFTQKSLSLSPGK 447
                                          ↑
                                        ΔΔAdp
```

FIG. 2A

```
IMGT        1          10         20         30         40         50         60
EU          341        350        360        370        380        390        400
            |          |          |          |          |          |          |
hIgG1       GQPREPQVYT LPPSRDELTK NQVSLTCLVK GFYPSDIAVE WESNGQPENN YKTTPPVLDS
hIgG1ΔAdp   GQPREPQVYT LPPSRDELTK NQVSLTCLVK GFYPSDIAVE WESNGQPENN YKTTPPVLDS
hIgG2       GQPREPQVYT LPPSREEMTK NQVSLTCLVK GFYPSDIAVE WESNGQPENN YKTTPPMLDS
hIgG2ΔAdp   GQPREPQVYT LPPSREEMTK NQVSLTCLVK GFYPSDIAVE WESNGQPENN YKTTPPMLDS
hIgG4       GQPREPQVYT LPPSQEEMTK NQVSLTCLVK GFYPSDIAVE WESNGQPENN YKTTPPVLDS
hIgG4ΔAdp   GQPREPQVYT LPPSQEEMTK NQVSLTCLVK GFYPSDIAVE WESNGQPENN YKTTPPVLDS
hIgG3       GQPREPQVYT LPPSREEMTK NQVSLTCLVK GFYPSDIAVE WESSGQPENN YNTTPPMLDS

IMGT        61         70         80         90         100        107
EU          401        410        420        430        440        447
            |          |          |          |          |          |
hIgG1       DGSFFLYSKL TVDKSRWQQG NVFSCSVMHE ALHNHYTQKS LSLSPGK    (SEQ ID NO:1)
hIgG1ΔAdp   DGSFFLYSKL TVDKSRWQQG NVFSCSVMHE ALHNRFTQKS LSLSPGK   (SEQ ID NO:2)
hIgG2       DGSFFLYSKL TVDKSRWQQG NVFSCSVMHE ALHNHYTQKS LSLSPGK   (SEQ ID NO:3)
hIgG2ΔAdp   DGSFFLYSKL TVDKSRWQQG NVFSCSVMHE ALHNRFTQKS LSLSPGK   (SEQ ID NO:4)
hIgG4       DGSFFLYSRL TVDKSRWQEG NVFSCSVMHE ALHNHYTQKS LSLSLGK   (SEQ ID NO:5)
hIgG4ΔAdp   DGSFFLYSRL TVDKSRWQEG NVFSCSVMHE ALHNRFTQKS LSLSLGK   (SEQ ID NO:6)
hIgG3       DGSFFLYSKL TVDKSRWQQG NIFSCSVMHE ALHNRFTQKS LSLSPGK   (SEQ ID NO:7)
```

FIG. 3

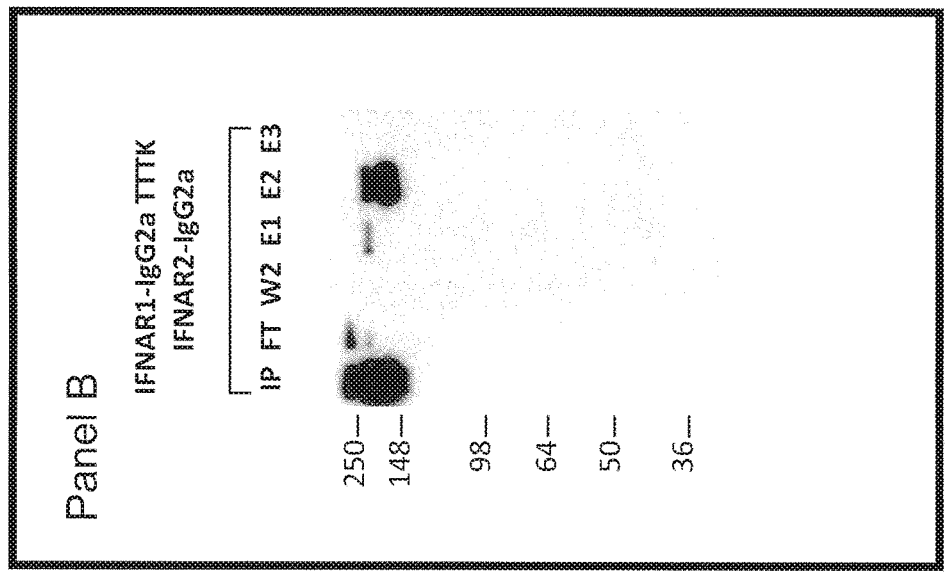
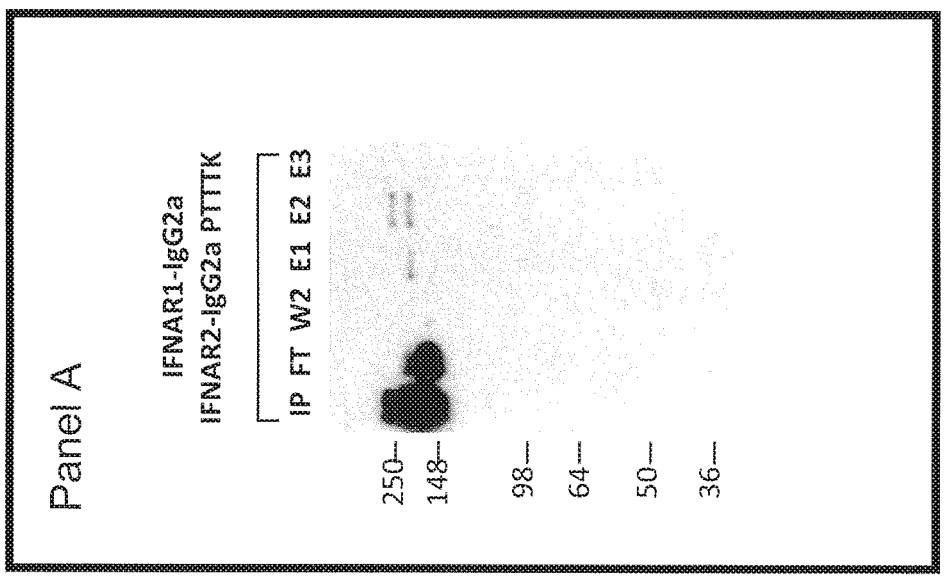
FIG. 9

READILY ISOLATED BISPECIFIC ANTIBODIES WITH NATIVE IMMUNOGLOBULIN FORMAT

CROSS REFERENCE

This application is a divisional of U.S. patent application Ser. No. 14/034,906 filed 24 Sep. 2013, which is a divisional application of non-provisional application Ser. No. 12/823,838 filed 25 Jun. 2010 (now U.S. Pat. No. 8,586,713), which claims the benefit under 35 U.S.C. § 119(e) of U.S. Provisional Patent Application No. 61/220,687 filed 26 Jun. 2009, all of which are incorporated by reference herein in their entirety.

FIELD OF INVENTION

The invention concerns antigen-binding proteins or antibodies having heterodimers of heavy chains, i.e., two immunoglobulin heavy chains that differ by at least one amino acid, that allows isolation of the antigen-binding protein based on a differential affinity of an immunoglobulin heavy chain and a modified or mutated immunoglobulin heavy chain toward an affinity reagent. The invention also concerns antigen-binding proteins (including bispecific antibodies) that have IgG CH2 and CH3 regions with different affinities with respect to Protein A that allows rapid isolation by differential binding of the IgG regions to Protein A.

BACKGROUND

Antibodies are multifunctional molecules, carrying a unique binding specificity for a target antigen, as well as the capacity to interact with the immune system via mechanisms that are antigen-independent. Many currently used biological therapeutics for cancer are monoclonal antibodies directed against antigens that are typically overexpressed on the targeted cancer cell. When such antibodies bind tumor cells, they may trigger antibody-dependent cellular cytotoxicity (ADCC) or complement-dependent cytotoxicity (CDC). Unfortunately, cancerous cells often develop mechanisms to suppress these normal immune responses.

In recent years, efforts have been underway to develop antibody-like therapeutics that have more than one antigen binding specificity, e.g., bispecific antibodies. In the case of cancer therapies, multi-specific formats could allow the possibility of using, e.g., one specificity to target the molecule to a tumor cell antigen, the other specificity to trigger a response that is not normally available to the immune system. Bispecific antibodies may also find use as surrogate ligands for two-component heterodimeric receptor systems that are normally activated by their natural ligand when it binds to and brings together both components.

Numerous formats have been developed in the art to address therapeutic opportunities afforded by molecules with multiple binding specificities. Ideally, such molecules should be well-behaved proteins that are easy to produce and purify, and possess favorable in vivo properties, e.g., pharmacokinetics appropriate for an intended purpose, minimal immunogenicity, and, if desirable, effector functions of conventional antibodies.

The most straightforward way of producing a bispecific antibody (expressing two distinct antibodies in a single cell) gives rise to multiple species, because the respective heavy chains form both homo- and heterodimers, but only the heterodimers are desired. Also, the light and heavy chains may pair inappropriately. Several examples of formats that attempt to address these problems in different ways are described below.

One format, used for Bispecific T cell Engager (BiTE) molecules (see, e.g., Wolf, E. et al. (2005) Drug Discovery Today 10:1237-1244)), is based on single chain variable fragment (scFv) modules. An scFv consists of an antibody's light and heavy chain variable regions fused via a flexible linker, which generally can fold appropriately and so that the regions can bind the cognate antigen. A BiTE concatenates two scFv's of different specificities in tandem on a single chain (see FIG. 1A). This configuration precludes the production of molecules with two copies of the same heavy chain variable region. In addition, the linker configuration is designed to ensure correct pairing of the respective light and heavy chains.

The BiTE format has several disadvantages. First, scFv molecules are notorious for their tendency to aggregate. And although the immunogenicity of scFv linkers is reputedly low, the possibility of generating antibodies against a BiTE cannot be ruled out. The absence of an Fc portion in the BiTE format also makes its serum half-life very short, and this necessitates the complication of frequent repeated administrations or continuous infusion via a pump. Finally, the absence of an Fc also implies the absence of Fc-mediated effector functions, which may be beneficial in some circumstances.

A second format (FIG. 1B) is a hybrid of a mouse and a rat monoclonal antibody, and relies on a modification of conventional Protein A affinity chromatography (see, e.g., Lindhofer, H. et al. (1995) J. Immunol. 155:219-225)). In this format, a mouse IgG2a and a rat IgG2b antibody are produced together in the same cell (e.g., either as a quadroma fusion of two hybridomas, or in engineered CHO cells). Because the light chains of each antibody associate preferentially with the heavy chains of their cognate species, only three distinct species of antibody can be assembled: the two parental antibodies, and a heterodimer of the two antibodies comprising one heavy/light chain pair of each, associating via their Fc portions. The desired heterodimer can be easily purified from this mixture because its binding properties to Protein A are different from those of the parental antibodies: rat IgG2b does not bind to protein A, whereas the mouse IgG2a does. Consequently, the mouse-rat heterodimer binds to Protein A but elutes at a higher pH than the mouse IgG2a homodimer, and this makes selective purification of the bispecific heterodimer possible. As with the BiTE format, this hybrid format has two monovalent antigen binding sites.

The disadvantage of the mouse/rat hybrid is that because it is non-human, it is likely to provoke an immune response in the patient, which could have deleterious side effects (e.g. "HAMA" or "HARA" reactions), and/or neutralize the therapeutic.

A third format, referred to as "knobs-into-holes" (FIG. 1C), has been discussed in the prior art as potentially useful for the production of bispecific antibodies (U.S. Pat. No. 7,183,076). In this strategy, the Fc portions of two antibodies are engineered to give one a protruding "knob", and the other a complementary "hole." When produced in the same cell, the heavy chains are said to preferentially form heterodimers rather than homodimers, by association of the engineered "knobs" with the engineered "holes." Issues of correct light-heavy chain pairing are addressed by choosing antibodies that have different specificities but employ identical light chains.

The disadvantage of this format is that the "knobs-into-holes" strategy can result in production of a significant amount of undesirable homodimers, thus necessitating further purification steps. This difficulty is exacerbated by the fact that the contaminating species are nearly identical to the desired species in many of their properties. The engineered forms may also potentially be immunogenic, because the mutations producing the "knobs" and "holes" introduce foreign sequences.

There remains a need for a bispecific antibody format, in particular for therapeutic applications, that minimizes some or all of the disadvantages mentioned above.

BRIEF DESCRIPTION OF THE FIGURES

FIG. 1(A-C) illustrates three bispecific antibody formats: (FIG. 1A) Bispecific T cell Engager (BiTE); (FIG. 1B) Mouse-Rat Hybrid; and, (FIG. 1C) Knobs-into-Holes with a common light chain.

FIG. 2(A-B) illustrates the FcΔAdp modification: (FIG. 2A) Alignment of Fc regions of human IgG1 (SEQ ID NO:1) and IgG3 (SEQ ID NO:3), showing boxed FcΔAdp modification.

FIG. 3 illustrates an alignment of human CH3 domains (employing IMGT exon numbering and EU numbering) of IgG1, IgG2, and IgG4, with and without the ΔAdp dipeptide modification, as well as IgG3.

FIG. 9 shows results for expression experiments using different mFc heterodimers. Panel A: Western blot of pH separation of heterodimeric mIgG2a/mIgG2aPTTTK from homodimeric mIgG2a and homodimeric IgG2aPTTTK; Panel B: Western blot of pH separation of heterodimeric mIgG2a/mIgG2aTTTK from homodimeric mIgG2a and homodimeric IgG2aTTTK; IP=input; FT=flow through; W2=second wash (1×PBS pH 7.2); E1=first elution (20 mM Na citrate, 1 M NaCl pH 5.5); E2=second elution (20 mM Na citrate, 1 M NaCl; 57% pH 5.5+43% pH 2.6); E3=third elution (20 mM Na citrate, 1 M NaCl pH 2.6).

SUMMARY

Figure 2B:
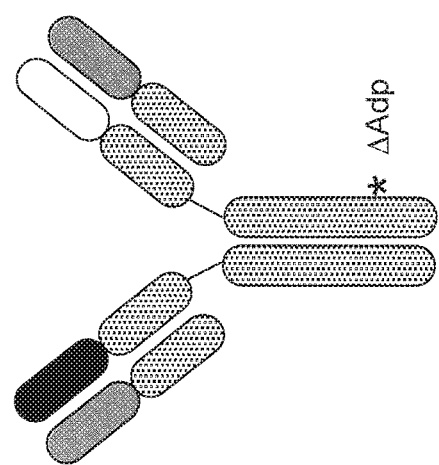
(FIG. 2B) a schematic representation of an FcΔAdp bispecific antibody.

The invention is based at least in part on employing two immunoglobulin CH3 heavy chain constant domain sequences that differ by at least one amino acid in a bispecific antigen-binding protein. The at least one amino acid difference results in an improved ability to isolate the protein, because the difference results in a differential ability of the CH3 domain sequences to bind an affinity agent.

In one aspect, an antigen-binding protein is provided, comprising a first and a second polypeptide, the first polypeptide comprising, from N-terminal to C-terminal, a first antigen-binding region that selectively binds a first antigen, followed by a constant region that comprises a first CH3 region of a human IgG selected from IgG1 (SEQ ID NO:1), IgG2 (SEQ ID NO:3), IgG4 (SEQ ID NO:5), and a combination thereof; and, a second polypeptide comprising, from N-terminal to C-terminal, a second antigen-binding region that selectively binds a second antigen, followed by a constant region that comprises a second CH3 region of a human IgG selected from IgG1, IgG2, IgG4, and a combination thereof, wherein the second CH3 region comprises a modification that reduces or eliminates binding of the second CH3 domain to protein A.

In one embodiment, the second CH3 region comprises an 95R modification (by IMGT exon numbering; 435R by EU numbering). In another embodiment, the second CH3 region further comprises a 96F modification (IMGT; 436F by EU). In specific embodiments, the second CH3 region is selected from SEQ ID NO:2, SEQ ID NO:4, and SEQ ID NO:6.

In one embodiment, the second CH3 region is from a modified human IgG1 (SEQ ID NO:2), and further comprises a modification selected from the group consisting of D16E, L18M, N44S, K52N, V57M, and V82I (IMGT; D356E, L358M, N384S, K392N, V397M, and V422I by EU).

In one embodiment, the second CH3 region is from a modified human IgG2 (SEQ ID NO:4), and further comprises a modification selected from the group consisting of N44S, K52N, and V82I (IMGT; N384S, K392N, and V422I by EU).

In one embodiment, the second CH3 region is from a modified human IgG4 (SEQ ID NO:6), and further comprises a modification selected from the group consisting of Q15R, N44S, K52N, V57M, R69K, E79Q, and V82I (IMGT; Q355R, N384S, K392N, V397M, R409K, E419Q, and V422I by EU).

In one embodiment, the CH3 domain is a chimeric domain that comprises sequences of two or more of human IgG1, human IgG2, human IgG3, and human IgG4.

In one embodiment, the CH3 domain is from human IgG1, human IgG2, or human IgG4, and the antigen-binding protein further comprises a CH1 domain and a CH2 domain, wherein the CH1 domain and the CH2 domain are independently selected from the group consisting of a human IgG1 CH1 or CH2 domain, a human IgG2 CH1 or CH2 domain, or a chimeric human/human IgG1/IgG2 or a chimeric human/human IgG1/IgG3 or a chimeric human/human IgG2/IgG3 domain or a chimeric human/human IgG1/IgG4 or a chimeric IgG3/IgG4 or a chimeric IgG2/IgG4 domain. In a specific embodiment, the chimeric IgG1/IgG2, IgG1/IgG3, IgG2/IgG3, IgG1/IgG4, IgG3/IgG4, and IgG2/IgG4 domains are non-immunogenic or substantially non-immunogenic in a human.

In one embodiment, the antigen-binding protein further comprises an immunoglobulin light chain. In one embodiment the immunoglobulin light chain is selected from a human lambda and a human kappa light chain.

In one embodiment, the first and the second antigen-binding regions each comprise at least one CDR, in another embodiment, at least two CDRs, in another embodiment, each comprises three CDRs. In a specific embodiment, the CDRs are from an immunoglobulin heavy chain. In another specific embodiment, the heavy chain is a human heavy chain.

In one embodiment, the first antigen-binding region comprises a first immunoglobulin heavy chain variable domain, and the second antigen-binding region comprises a second immunoglobulin heavy chain variable domain.

In one embodiment, the first and the second immunoglobulin heavy chain variable domains are independently selected from a mouse, rat, hamster, rabbit, monkey, ape, and human domain.

In one embodiment, the first and the second immunoglobulin heavy chain variable domains independently comprise a human CDR, a mouse CDR, a rat CDR, a rabbit CDR, a monkey CDR, an ape CDR, and a humanized CDR. In one embodiment, the CDR is human and is somatically mutated.

In one embodiment, the first and the second immunoglobulin heavy chain variable domain comprises a human framework region (FR). In one embodiment, the human FR is a somatically mutated human FR.

In one embodiment, the first and/or the second antigen-binding regions are obtained by screening a phage library comprising antibody variable regions for reactivity toward an antigen of interest. In another embodiment, the first and/or the second antigen-binding regions are obtained by immunizing a non-human animal such as a mouse, a rat, a rabbit, a monkey, or an ape with an antigen of interest and identifying an antibody variable region nucleic acid sequence encoding a variable region specific for the antigen of interest. In a specific embodiment, the non-human animal comprises one or more human immunoglobulin variable region genes. In another specific embodiment, the one or more human immunoglobulin variable region genes are present in the non-human animal extrachromosomally, as a replacement at an endogenous immunoglobulin locus, or as a transgene randomly integrated into the genome of the non-human animal. In one embodiment, the first and/or the second antigen-binding regions are obtained from a hybridoma or a quadroma, in another embodiment from screening immune cells of an immunized non-human animal using cell sorting.

In one embodiment, the antigen-binding protein is a bispecific antibody. In one embodiment, the bispecific antibody is a fully human bispecific antibody and has an affinity for each epitope, independently, in the micromolar, nanomolar, or picomolar range.

In one embodiment, the antigen-binding protein is non-immunogenic or substantially non-immunogenic in a human. In a specific embodiment, the antigen-binding protein lacks a non-native human T-cell epitope. In one embodiment, the modification of the CH3 region is non-immunogenic or substantially non-immunogenic in a human. In a specific embodiment, the modification of the CH3 region does not result in a non-native human T-cell epitope.

In one embodiment, the antigen-binding protein comprises a heavy chain, wherein the heavy chain is non-immunogenic or substantially non-immunogenic in a human. In one embodiment, the heavy chain has an amino acid sequence that does not contain a non-native T cell epitope. In one embodiment, the heavy chain comprises an amino acid sequence whose proteolysis cannot form an amino acid sequence of about 9 amino acids that is immunogenic in a human. In a specific embodiment, the human is a human being treated with the antigen-binding protein. In one embodiment, the heavy chain comprises an amino acid sequence whose proteolysis cannot form an amino acid sequence of about 13 to about 17 amino acids that is immunogenic in a human. In a specific embodiment, the human is a human being treated with the antigen-binding protein.

In one aspect, a bispecific binding protein comprising a CH2 and/or CH3 modification as described herein is provided, wherein the bispecific binding protein comprises a first binding moiety that specifically recognizes an antigen on a B cell, and a second binding moiety that specifically recognizes an antigen on a T cell.

In one embodiment, the binding protein is a bispecific antibody. In a specific embodiment, the bispecific antibody comprises a human IgG1 heavy chain and a human IgG1ΔAdp heavy chain. In one embodiment, the first binding moiety is a human heavy chain variable domain that specifically recognizes CD20. In one embodiment, the second binding moiety is a human heavy chain variable domain that specifically recognizes CD3. In one embodiment, the bispecific antibody exhibits an EC50 in a Raji killing assay of about $2.8-3.2\times10^{-12}$ M, or about $2.8-3.0\times10^{-12}$ M, and exhibits no more than about 1-10%, or 1-5%, bystander killing in a bystander cell killing assay, wherein the bystander cell does not comprise a CD20 epitope. In a specific embodiment, the bystander cell is a 293 cell. In another specific embodiment, bystander cell killing in the assay is measured across a concentration of bispecific antibody of about $10^{-8}$ M to about $10^{-14}$ M.

In one aspect, a method for making a bispecific antibody is provided, comprising: obtaining a nucleic acid sequence encoding a first immunoglobulin heavy chain comprising a first variable domain that recognizes a first epitope, wherein the first immunoglobulin heavy chain comprises an IgG1, IgG2, or IgG4 isotype constant domain, or a chimeric isotype constant domain thereof; obtaining a second nucleic acid sequence encoding a second immunoglobulin heavy chain comprising a second variable domain that recognizes a second epitope, wherein the second immunoglobulin heavy chain comprises an IgG1, IgG2, or IgG4 isotype constant domain, or a chimeric isotype constant domain thereof, that comprises a modification in its CH3 domain that eradicates or reduces binding to Protein A; obtaining a third nucleic acid sequence encoding an immunoglobulin a light chain that pairs with the first and the second immunoglobulin heavy chain; introducing the first, second, and third nucleic acid sequences into a mammalian cell; allowing the cell to express an immunoglobulin, and isolating the immunoglobulin using Protein A.

In one embodiment, the cell is selected from a CHO, COS, 293, HeLa, and a retinal cell expressing a viral nucleic acid sequence (e.g., a PERC.6™ cell).

In one aspect, a bispecific antigen-binding protein is provided that comprises a first specificity that binds an antigen and a second specificity that activates a receptor, wherein the bispecific antigen-binding protein comprises a first polypeptide comprising a first IgG1, IgG2, or IgG4 CH3 domain that comprises a Protein A-binding determinant, and a second polypeptide comprising a second IgG1, IgG3, or IgG4 CH3 domain that lacks the Protein A-binding determinant.

In one embodiment, the second specificity that activates the receptor binds the receptor with a $K_D$ that is in the molar, millimolar, micromolar, nanomolar, or picomolar range.

In one embodiment, the second specificity binds a receptor selected from a G-protein coupled receptor, a receptor tyrosine kinase, an integrin, and a toll-like receptor.

In one embodiment, the second specificity contacts the receptor and causes the receptor or a subunit or a protein physically associated therewith to undertake phosphorylation of a serine, threonine, or tyrosine; cause cyclization of a nucleotide (e.g., cAMP, cADP, or cGMP); cause production of a phosphatidylinositol or derivative thereof (e.g., IP3 or PIPS); cause production of a lipid second messenger (e.g., diacylclycerol, ceramide, lysophosphatidic acid, an eicosanoid); cause dephosphorylation (e.g., phosphatase activity); cause phosphorylation of a lipid to form a second messenger; cause hydrolysis of a second messenger; cause proteolysis; cause redox signaling; cause translocation of a protein to a cellular organelle (e.g., to the nucleus); cause the receptor to aggregate (with itself) to form homo- or (with other receptors) to form heteromultimers; or cause the opening or closing of a transmembrane channel.

In one aspect, a method for making a bispecific antibody is provided, comprising: isolating a bispecific antibody of interest from a quadroma, wherein the bispecific antibody of interest comprises a first heavy chain that is an IgG1, IgG2, or IgG4 isotype, a second heavy chain that is an IgG1, IgG2, or IgG4 isotype having a constant domain that comprises a modification in its CH3 domain that eradicates or reduces binding to Protein A, wherein the bispecific antibody of interest is isolated using Protein A.

In one aspect, a method for making a bispecific antibody is provided, comprising a step of isolating from a disrupted cell or a mixture of antibodies a bispecific antibody having differentially modified IgG1, IgG2, or IgG4 CH3 domains, wherein the differentially modified CH3 domains are non-immunogenic or substantially non-immunogenic in a human, and wherein the modification results in a bispecific antibody with a heterodimeric heavy chain whose monomers have a differential affinity for Protein A, and the bispecific antibody is isolated from the disrupted cell or the mixture using Protein A.

In one embodiment, the bispecific antibody is isolated using a Protein A affinity support, wherein the bispecific antibody elutes at a pH between about 3.9 to about 4.4, about 4.0 to about 4.3, about 4.1 to about 4.2, or at about pH 4.2. In one embodiment, the bispecific antibody elutes at a pH of about 4, 4.1, 4.2, 4.3, 4.4, or 4.5.

In one embodiment, the bispecific antibody is isolated using a Protein A affinity support and a pH gradient or step, wherein the pH gradient or step includes an ionic modifier. In a specific embodiment, the ionic modifier is present at a concentration of about 0.5 to about 1.0 molar. In a specific embodiment, the ionic modifier is a salt. In one embodiment, the ionic modifier is selected from the group consisting of beryllium, lithium, sodium, and potassium salts of acetate; sodium and potassium bicarbonates; lithium, sodium, potassium, and cesium carbonates; lithium, sodium, potassium, cesium, and magnesium chlorides; sodium and potassium fluorides; sodium, potassium, and calcium nitrates; sodium and potassium phosphates; and calcium and magnesium sulfates. In a specific embodiment, the ionic modifier is a halide salt of an alkaline metal or alkaline earth metal. In a specific embodiment, the ionic modifier is sodium chloride.

In one aspect, a binding protein comprising an Fc, wherein the Fc comprises a first CH3 domain that is modified as described herein and a second CH3 that is not modified, so as to form a heterodimeric Fc, wherein the differential modification results in the binding protein eluting from a protein A affinity material at 0.5, 0.6, 0.7, 0.8, 0.9, 1.0, 1.2, 1.3, or 1.4 pH unit(s) higher than a corresponding binding protein that lacks the differential modification.

In one embodiment, the differentially modified binding protein elutes at a pH of about 4.2, whereas the unmodified binding protein elutes at a pH of about 3. In one embodiment the differentially modified binding protein elutes at a pH of about 4.5, whereas the unmodified binding protein elutes at a pH of about 3.5. In one embodiment, the differentially modified binding protein elutes at a pH of about 4, whereas the unmodified binding protein elutes at a pH of about 2.8-3.5, 2.8-3.2, or 2.8-3. In one embodiment, the differentially modified binding protein elutes at a pH of about 4.2, whereas the unmodified binding protein elutes at a pH of about 2.8. In one embodiment, the differentially modified binding protein elutes at a pH of about 4.4, whereas the unmodified binding protein elutes at a pH of about 3.6. In these embodiments, "unmodified" refers to lack of a modification at 435 (EU numbering), or lack of a modification at 435 and 436 (EU numbering), on both of the CH3 domains.

Any of the embodiments and aspects described herein can be used in conjunction with one another, unless otherwise indicated or apparent from the context. Other embodiments will become apparent to those skilled in the art from a review of the ensuing description.

DETAILED DESCRIPTION

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, particular methods and materials are now described. All publications mentioned are hereby incorporated by reference.

The term "antibody", as used herein, includes immunoglobulin molecules comprised of four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to those antibodies having a binding affinity to their target of at least $10^{-9}$ M, at least $10^{-10}$ M; at least $10^{-11}$ M; or at least $10^{-12}$ M, as measured by surface plasmon resonance, e.g., BIACORE™ or solution-affinity ELISA.

The phrase "antigen-binding protein" includes a protein having at least one CDR and that is capable of selectively recognizing an antigen, i.e., is capable of binding an antigen with a $K_D$ that is at least in the micromolar range. Therapeutic antigen-binding proteins (e.g., therapeutic antibodies) frequently require a $K_D$ that is in the nanomolar or the picomolar range. "Antigen-binding protein" also includes a protein comprising a first and a second CH3 domain as described herein and a first protein or ligand recognition domain and a second protein or ligand recognition domain, wherein the first protein or ligand recognition domain and the second protein or ligand recognition domain each independently recognize the same protein or ligand, or together recognize the same protein or ligand, or each independently recognize a different protein or ligand. One example of such protein is an immunoadhesin, comprising a fusion protein (hetero- or homo-) dimer wherein the polypeptides of the dimer are fusion polypeptides that comprise a receptor component or a ligand component, wherein the ligand component comprises an amino acid sequence that binds a receptor.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen (e.g., recognizing the antigen with a $K_D$ in the micromolar, nanomolar, or picomolar range), that is capable of expressing and secreting from a cell, and that comprises at least one CDR.

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind a Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

The phrase "ionic modifier" includes moieties that reduce the effect of, or disrupt, non-specific (i.e., non-affinity) ionic interactions between proteins. "Ionic modifiers" include, for example, salts, ionic combinations of Group I and Group II metals with acetate, bicarbonate, carbonate, a halogen (e.g., chloride or fluoride), nitrate, phosphate, or sulfate. A non-limiting illustrative list of "ionic modifiers" includes beryllium, lithium, sodium, and potassium salts of acetate; sodium and potassium bicarbonates; lithium, sodium, potassium, and cesium carbonates; lithium, sodium, potassium, cesium, and magnesium chlorides; sodium and potassium fluorides; sodium, potassium, and calcium nitrates; sodium and potassium phosphates; and calcium and magnesium sulfates. "Ionic modifiers" include those moieties that affect ionic interactions that, upon addition to a pH gradient or step, or upon equilibration of a Protein A support in an "ionic modifier" and application of a pH step or gradient, results in a broadening of pH unit distance between elution of a homodimeric IgG and a heterodimeric IgG (e.g., a wild-type human IgG and the same IgG but bearing one or more modifications of its CH3 domain as described herein). A suitable concentration of an "ionic modifier" can be determined by its concentration employing the same column, pH step or gradient, with increasing concentration of "ionic modifier" until a maximal pH distance is reached at a given pH step or pH gradient.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains that can be used with this invention include those, e.g., that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

The phrase "micromolar range" is intended to mean 1-999 micromolar; the phrase "nanomolar range" is intended to mean 1-999 nanomolar; the phrase "picomolar range" is intended to mean 1-999 picomolar.

The phrase "somatically mutated" includes reference to a nucleic acid sequence from a B cell that has undergone class-switching, wherein the nucleic acid sequence of an immunoglobulin variable region (e.g., a heavy chain variable domain or including a heavy chain CDR or FR sequence) in the class-switched B cell is not identical to the nucleic acid sequence in the B cell prior to class-switching, such as, for example, a difference in a CDR or framework nucleic acid sequence between a B cell that has not undergone class-switching and a B cell that has undergone class-switching. "Somatically mutated" includes reference to nucleic acid sequences from affinity-matured B cells that are not identical to corresponding sequences in B cells that are not affinity-matured (i.e., sequences in the genome of germline cells). The phrase "somatically mutated" also includes reference to a nucleic acid sequence from a B cell after exposure of the B cell to an antigen of interest, wherein the nucleic acid sequence differs from the corresponding nucleic acid sequence prior to exposure of the B cell to the antigen of interest. The phrase "somatically mutated" refers to sequences from antibodies that have been generated in an animal, e.g., a mouse having human immunoglobulin variable region nucleic acid sequences, in response to an antigen challenge, and that result from the selection processes inherently operative in such an animal.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

Bispecific Antibodies with Modified IgG CH3 Regions

The inventors have developed a novel format that combines a common light chain strategy with an implementation of a selective Protein A purification scheme that can be used with human antibody components.

It has been previously noted (Lindhofer, H. et al. (1995) J. Immunol. 155:219-225)) that because human IgG3 does not to bind to Protein A, it can potentially be used together with any of the other three human IgG subclasses in a purification strategy similar to the one used for mouse-rat hybrids. However, although the sequences of all four human IgG subclasses are highly homologous, it is not known how readily the Fc portions of IgG1, IgG2, and IgG4 form heterodimers with IgG3; even merely preferential formation of homodimers would have a negative impact on total yields of the desired heterodimers under certain circumstances (e.g., isolation from quadromas). Additional modifications may also be necessary to compensate for the difference between the hinge region of IgG3 and those of the other subclasses. It would also be preferable, in some circumstances, not to require the presence of the full IgG3 Fc, because of potential impact on effector functions.

The inventors have therefore devised a "minimal" format that exploits a fortuitously simple determinant of Protein A binding. It has been reported (Jendeberg, L. et al. (1997) J. Immunological Meth. 201:25-34)) that the inability of IgG3 to bind Protein A is determined by a single amino acid residue, Arg435 (EU numbering; Arg95 by IMGT), which corresponding position in the other IgG subclasses is occupied by a histidine residue. It is therefore possible, instead of IgG3, to use an IgG1 sequence in which His435 is mutated to Arg. Thus, a single point mutation in IgG1 should be sufficient to create the different binding affinities amenable to a new purification scheme. This modification will be referred to as IgG1ΔA, to denote its inability to bind Protein A (and, similarly, IgG2ΔA and IgG4ΔA—or more generally, FcΔA).

However, the specified point mutation introduces a novel peptide sequence across the mutation, which could potentially be immunogenic. The point mutation could, in theory, be loaded onto an MHC class II molecule and presented to T cells, and consequently elicit an immune response. To avoid this pitfall, a dipeptide mutation, H435R/Y436F (EU numbering; H95R/Y96F by IMGT) can be used. The resulting sequence in the vicinity of the alteration is identical to that of IgG3 (see FIG. 2A), and would therefore be expected to be immunologically "invisible," because there would be no non-native short peptides available for presentation to T cells. It has been reported that this double mutant still does not bind Protein A (Jendeberg, L. et al. (1997) J. Immunological Meth. 201:25-34). Finally, the dipeptide mutation does not include any of the residues that form the Fc dimer interface, so it is unlikely to interfere with the formation of heterodimers. This dipeptide mutation is designated as "IgG1ΔAdp" (and, similarly, IgG2ΔAdp, IgG4ΔAdp, and FcΔAdp). Placement of the dipeptide modification in IgG1, IgG2, and IgG4 are indicated in FIG. 3 in the sequences denoted IgG1ΔAdp, IgG2ΔAdp, and IgG4ΔAdp, shown with wild-type human IgG CH3 domain sequences, as well as hIgG3, showing IMGT exon numbering and EU numbering.

The FcΔAdp modification does not include any of the residues believed to form the Fc dimer interface, so the FcΔAdp modification is unlikely to interfere with the formation of heterodimers. Because the FcΔAdp is so minimal, it can likely be incorporated into other engineered Fc forms as well. IgG2ΔAdp and IgG4ΔAdp may be advantageous in situations in which the effector functions (or lack thereof) associated with each of the latter are desired.

In summary, the bispecific antibody format described above includes two antibodies of different specificity that use the same light chain, wherein the Fc region of one of them is modified to the FcΔAdp format (see FIG. 2B). Its configuration is that of a natural human antibody, and should therefore share its favorable properties, including a low propensity to aggregate, in vivo stability, minimal immunogenicity, biodistribution properties similar to those of antibodies, good pharmacokinetics, and, optionally, effector functions. Methods for isolating such bispecific antibodies are provided that are relatively rapid and simple in execution.

Bispecific Binding Proteins with Modified Mouse IgG CH Regions

The inventors have devised a method for readily isolating a binding protein comprising an immunoglobulin heavy chain (or functional CH2 and CH3-containing fragment thereof) that is heterodimeric with respect to one or more amino acids in the CH3 domain. A careful selection of modifications of a mouse IgG CH domain and application of a particular separation technology confer the ability to readily isolate a binding protein comprising two differentially modified mouse CH regions from homodimers and from heterodimers that do not contain the modifications.

Mouse IgG1, which contains a proline at 247, a threonine at 252, 254, and 256, and a lysine at 258, binds only weakly to protein A. Mouse IgG2a and IgG2b, however, contain different residues at those positions (with the exception of IgG2b positions 256 and 258), and mouse IgG2a and 2b bind well to protein A. Differentially modifying the CH regions of two mouse IgGs in a method for making an antibody that is heterodimeric for heavy chains would confer a differential protein A binding characteristic to such an antibody. In this way, a differential protein A isolation scheme is devised that allows for ready separation of a modified heterodimer from any mouse IgG homodimer, whether it is a homodimer of IgG1 (which would bind only quite weakly, if at all, to protein A), or a homodimer of mouse IgG2a, a homodimer of mouse IgG2b, or a heterodimer of IgG2a/IgG2b. For example, a bispecific antibody having two different heavy chain variable domains but the same isotype, e.g., IgG2a, can be expressed in a suitable expression system that employs the heavy chain sequences, wherein only one of the IgG2a CH regions is modified to reduce or eliminate a protein A binding determinant. In this way, only one of the IgG2a CH regions will exhibit a substantial affinity for protein A, and any antibody formed from a dimer of an unmodified IgG2a and a modified IgG2a will be readily isolated from the modified heterodimer.

In various embodiments, an antibody wherein a single CH region of an Fc dimer comprises the modified CH region, whereas the other CH of the Fc dimer lacks them. The mouse IgG CH region is modified to comprise particular amino acids at particular positions (EU numbering), selected from the group consisting of: 252T, 254T, and 256T; 252T, 254T, 256T, and 258K; 247P, 252T, 254T, 256T, and 258K; 435R and 436F; 252T, 254T, 256T, 435R, and 436F; 252T, 254T, 256T, 258K, 435R, and 436F; 24tP, 252T, 254T, 256T, 258K, 435R, and 436F; and, 435R. In a specific embodiment, a particular group of modifications is made, selected from the groups consisting of: M252T, S254T, S256T; M252T, S254T, S256T, I258K; I247P, M252T, S254T, S256T, I258K; H435R, H436F; M252T, S254T, S256T, H435R, H436F; M252T, S254T, S256T, I258K, H435R, H436F; I247P, M252T, S254T, S256T, I258K, H435R, H436F; and, H435R.

Heterodimeric mouse IgG-based binding proteins can be used for a variety of applications. For example, they allow for a method of isolating bispecific antibodies with mouse constant domains, wherein the modifications do not interfere or do not substantially interfere with binding of the antibody to one or more mouse Fc receptors, such that the antibody can participate, e.g., in ADCC or CDC and also bind two or more epitopes on the same or different target.

In one aspect a method for isolating a binding protein comprising a first mouse IgG CH region and a second mouse IgG CH region, wherein the first IgG CH region is modified (but not the second IgG CH region) so as to reduce or eliminate protein A binding affinity of the first mouse IgG CH region but not the second mouse IgG CH region, and wherein the binding protein comprises a first binding moiety that binds a first epitope and a second binding moiety that binds a second epitope.

In one embodiment, the modification does not alter or does not substantially alter binding affinity of the binding protein to an Fc receptor. In one embodiment, the binding protein comprises a modification that increases or decreases affinity for the binding protein to an Fc receptor.

In one embodiment, the modification does not alter or does not substantially alter the serum half-life of the binding protein in a mouse comprising native mouse FcγR receptors and/or a native mouse FcRn, as compared with a corresponding binding protein that lacks the modification.

In one embodiment, the modification does not alter or does not substantially alter the serum half-life of the binding protein in a mouse that comprises a replacement of native mouse high and low affinity FcγR receptors and/or an FcRn receptor, as compared with a corresponding binding protein that lacks the modification.

In one embodiment, the first and the second epitope are different and are on different cells or on different proteins. In one embodiment, the first epitope and the second epitope are different and are on the same cell or the same protein.

In one embodiment, the Fc receptor is selected from a high affinity Fc receptor, a low affinity Fc receptor, and a FcRn. In a specific embodiment, the Fc receptor is selected from one or more of a mouse FcRn, a mouse FcγR, a mouse FcγRIIB, a mouse FcγRIII, a mouse FcγRIV, and a combination thereof. In a specific embodiment, the Fc receptor is selected form one or more of a human FcRn, a human FcγR, a human FcγRIIB, a human FcγRIIC, a human FcγRIIIB, a human FcγRIIIA, a human FcγRIIA, and a combination thereof.

Immunogenicity

One advantage of many embodiments of the invention is the ability to employ the modification(s) to make a bispecific antibody that is both readily isolable based on differential binding to Protein A and is also non-immunogenic or substantially non-immunogenic in a human. This feature makes such embodiments particularly useful in making bispecific antibodies for human therapeutic use, and in making immunoadhesins, e.g., that are non-immunogenic or substantially non-immunogenic (employing human binding moieties, i.e., human receptor components and/or human ligands). This feature is associated with bispecific antibodies having CH3 domains with the H95R/Y96F (IMGT numbering) modifications of IgG1, IgG2, and IgG3, and those CH3 domains that contain further modifications that result in the position being modified reflecting a wild-type sequence of a different IgG isotype. Thus, although the modification is not found in nature associated with the particular IgG isotype, the modified sequence is locally identical with a wild-type sequence of a different IgG isotype, and the modification is not expected to be immunogenic or substantially immunogenic. It is also possible that a modification is non-immunogenic even if its sequence is not locally identical to any native sequence; such modifications would be equally useful. The minimal point mutation H95R (IMGT numbering), if non-immunogenic, would therefore be a suitable embodiment of the invention.

Thus, bispecific antibodies are provided that are non-immunogenic or substantially non-immunogenic in a human, with respect to their heavy chain constant domains, but nonetheless bear one or more differential modifications of the heavy chain constant domain, including a modification that results in a differential affinity of the heavy chain constant domains with respect to an affinity reagent (e.g., Protein A). The modifications comprise those disclosed herein. In a specific embodiment, the bispecific antibody that is non-immunogenic or substantially non-immunogenic in a human with respect to its CH3 domain, yet having differentially modified heavy chains is a human IgG1, IgG2, or IgG4 comprising a CH3 domain that comprises one of the following modifications (or, in another embodiment, consists essentially of one of the following modifications): H95R, or H95R and Y96F (IMGT numbering).

The bispecific antibodies are expected to be non-immunogenic, or substantially non-immunogenic, with respect to humans in whom tolerance to human IgG1, IgG2, and IgG4 isoforms has not been broken to any significant degree.

In particular, the FcΔAdp modification is expected to be immunologically "invisible" because the binding groove of MHC class II molecules accommodates a 9-mer that comprises the major determinant recognized by variable loops of the T cell receptor, so that peptides lacking any native 9-mer subsequence would appear unlikely to elicit an immune response. However, peptides longer than 9-mers (usually about 13- to 17mer) are bound by MHC class II, and it is possible that protruding segments may potentially influence binding. Therefore, additional modifications (over the FcΔAdp modification) that eliminate longer non-native sequences may further reduce potential for immunogenicity. One specific example is the modification V422I (EU; V82I by IMGT numbering), which extends the length of the minimal non-native peptide from 14 to 39 residues in IgG1ΔAdp, and to 43 residues in the analogously defined IgG2ΔAdp. Another example is the modification L445P (EU; L105P by IMGT numbering) in IgG4ΔAdp, which extends the length from 10 to 14 residues.

Pharmacokinetics

The binding site for Protein A overlaps with the binding site for the neonatal Fc receptor, FcRN, which is thought to be responsible for conferring a prolonged serum half-life to immunoglobulins. Modifications in the vicinity of the Protein A binding site, therefore, raise the possibility that the format proposed here could have a shorter serum half-life than those of IgG1, 2, and 4, given that human IgG3 has a shorter serum half-life (about 7 days) than the other IgG subclasses (about 21 days). Some Fc mutants affecting His435 have been shown not to bind FcRN, and have a shorter half-life in mice. However, pharmacokinetic analysis has shown that the serum half-life of the IgG1ΔA/IgG1 heterodimer is not appreciably different from that of the IgG1 homodimer (see Example 2). Thus the IgG1ΔAdp mutation has the advantage of ablating Protein A binding while still preserving the longer half-life of IgG1.

Accordingly, in one embodiment, a bispecific antigen-binding protein is provided that comprises a modification of a CH3 domain as described herein, wherein the antigen-binding protein displays a pharmacokinetic profile equivalent to the same bispecific antigen-binding protein that lacks the modification at the CH3 domain. In one embodiment, a bispecific antibody is provided that comprises an IgG1 ΔA/IgG1 heterodimeric Fc, wherein the bispecific antibody has a serum half-life that is about 1.5-fold, about 2-fold, about 2.5-fold, or about 3 fold higher than a bispecific antibody that is otherwise identical but comprises an IgG3 CH3 domain, or that is otherwise identical but comprises at least one IgG3 heavy chain. In one embodiment, a bispecific antibody is provided comprising an IgG1ΔA/IgG1 heterodimeric Fc, wherein the bispecific antibody exhibits a serum half-life that is about the same as that of the bispecific antibody without the IgG1ΔA modification (i.e., an IgG1 homodimeric bispecific antibody).

Immunoglobulin Heavy Chains

Immunoglobulin heavy chain variable regions that can be used to generate bispecific antibodies with desired characteristics (e.g., desired specificities, desired affinities, desired functionalities, e.g., blocking, non-blocking, inhibiting, activating, etc.) can be generated using any method known in the art. The desired heavy chains can then be constructed by cloning nucleic acid sequences containing the variable regions in constructs having the desired heavy chain constant regions described herein.

In one embodiment, the first heavy chain comprises a variable region that is encoded by a nucleic acid that is derived from the genome of a mature B cell of a first animal that has been immunized with a first antigen, and the first heavy chain specifically recognizes the first antigen. In a specific embodiment, the second heavy chain comprises a variable region that is encoded by a nucleic acid that is derived from the genome of a mature B cell of a second animal that has been immunized with a second antigen, and the second heavy chain specifically recognizes the second antigen.

In one embodiment, the first animal and/or the second animal is a genetically modified animal comprising an unrearranged human immunoglobulin heavy chain variable region. In one embodiment, the first animal and/or the second animal is a genetically modified animal comprising an unrearranged human immunoglobulin heavy chain variable region and a human immunoglobulin constant region. In one embodiment, the first animal and/or the second animal is a genetically modified mouse that comprises an unrearranged human immunoglobulin heavy chain variable region.

Immunoglobulin heavy chain variable region sequences can be obtained by any other method known in the art, e.g., by phage display, and sequences obtained thereby can be employed to make nucleic acid constructs to be joined to nucleic acids encoding any suitable heavy chain, e.g., heavy chains with modified CH3 domains as described herein, and placed in an expression construct and transferred to a cell that is capable of making the heavy chain, e.g., in the presence of a suitable light chain.

Immunoglobulin Light Chains

Bispecific antibodies comprising two heavy chains that recognize two different epitopes (or two different antigens) are more easily isolated where they can pair with the same light chain (i.e., light chains having identical variable and constant domains). A variety of methods are known in the art for generating light chains that can pair with two heavy chains of differing specificity, while not interfering or not substantially interfering with the selectivity and/or affinity of the heavy chain variable domain with its target antigen.

In approach, a light chain can be selected by surveying usage statistics for all light chain variable domains, identifying the most frequently employed light chain in human antibodies, and pairing that light chain with the two heavy chains of differing specificity.

In another approach, a light chain can be selected by observing light chain sequences in a phage display library (e.g., a phage display library comprising human light chain variable region sequences, e.g., a human ScFv library) and selecting the most commonly used light chain variable region from the library.

In another approach, a light chain can be selected by assaying a phage display library of light chain variable sequences using the heavy chain variable sequences of both heavy chains as probes. A light chain that associates with both heavy chain variable sequences is selected as a light chain for the heavy chains and allows binding and/or activation with respect to both epitopes.

In another approach, a light chain can be selected by combining known light chains with desired heavy chains and assaying the resulting bispecific antibody for binding specificity, affinity, and/or activation ability.

To the extent that a difficulty is encountered in any of the approaches for selecting a light chain (e.g., the light chain interferes with the binding of one or both of the heavy chains with its antigen, or the light chain fails to associate satisfactorily with one or both of the heavy chains), the light chain can be aligned with the heavy chains' cognate light chains, and modifications are made in the light chain to more closely match sequence characteristics common to the cognate light chains of both heavy chains. If the chances of immunogenicity need to be minimized, the modifications preferably result in sequences that are present in known human light chain sequences, such that proteolytic processing is unlikely to generate a T cell epitope based on parameters and methods known in the art for assessing the likelihood of immunogenicity (i.e., in silico as well as wet assays).

Antibodies and Binding Proteins

The compositions and methods are particularly useful in making human bispecific antibodies, i.e., bispecific antibodies comprising human constant and variable domains. In some embodiments human antibodies include those having heavy chain variable and heavy chain constant domains derived from human germline immunoglobulin sequences, in some embodiments derived from somatically mutated human immunoglobulin sequences (generated, e.g., in an animal that comprises human immunoglobulin gene sequences). In some embodiments the human variable and/or constant regions may include amino acid residues not encoded by human germline immunoglobulin sequences or encoded as the result of recombination and/or splicing for example in the CDRs and in particular CDR3. Human antibodies are not intended to include antibodies in which CDR sequences derived from the germline of another mammalian species, such as a mouse, have been grafted onto human framework sequences. Those antibodies are referred to as humanized or chimeric antibodies. Human antibodies do include those comprising mutations, e.g., introduced in vitro by random or site-specific mutagenesis, but the mutations are preferably non-immunogenic in a human.

The methods and compositions can be used to make chimeric antibodies, preferably non-immunogenic in a human, or of low immunogenicity. Chimeric antibodies are antibodies in which one of a heavy chain variable region or framework or CDR or heavy chain constant region or domain are from different species (e.g., human and mouse, or human and primate). In some embodiments, chimeric antibodies include antibodies having a heavy chain variable region of non-human origin (e.g., mouse) and a heavy chain constant region of human origin. In some embodiments, chimeric antibodies include antibodies having a heavy chain variable region of human origin and a heavy chain constant region of non-human (e.g., mouse) origin. In various embodiments, regions of mouse origin are identical or substantially identical to a mouse immunoglobulin germline sequence with or without somatic hypermutations. Chimeric antibodies also include antibodies having a light chain constant region that is identical or substantially identical to a human immunoglobulin germline sequence and a non-human (e.g., mouse) heavy chain or chimeric human/non-human heavy chain. Chimeric antibodies include antibodies having a light chain constant domain that is identical or substantially identical to a non-human (e.g., mouse) immunoglobulin germline sequence and a human or chimeric nonhuman/human heavy chain.

In some embodiments, the compositions and methods are for making an affinity-matured antibody. In some embodiments, an affinity-matured antibody comprises one or more alterations in one or more CDRs that result in higher affinity (e.g., $K_D$ in the nanomolar or picomolar range) of the antibody for its target antigen as compared to a substantially identical antibody that lacks the alteration(s). Affinity-matured antibodies can be made by any suitable method known in the art, e.g., by random or site-directed mutagenesis of CDRs and/or framework regions followed by affinity screening, VH domain shuffling, etc.

In some embodiments, the antibodies are neutralizing antibodies. Neutralizing antibodies include antibodies capable of neutralizing, inhibiting, or preventing an antigen's biological activity. Neutralizing antibodies include those that, upon binding an antigen, prevent or reduce the antigen's ability to act on a natural target of the antigen in vivo and in vitro. Examples of neutralizing antibodies include an antibody to a protein ligand of a biological receptor that prevents the ligand from binding the receptor, or an antibody to a biological receptor that prevents the receptor from binding its ligand, where ligand binding in the absence of the antibody causes the receptor to effect a change inside of a cell. Determining whether an antibody is a neutralizing antibody generally entails conducting a functional assay wherein the antibody's effect on the biological activity of the antigen is measured.

The methods and compositions of the invention are also useful in a variety of applications for antibodies and other binding proteins. A short description of some useful applications are provided here.

Bispecific binding proteins that comprise binding specificity toward a tumor antigen and a T-cell antigen can be made that target an antigen on a cell, e.g., CD20, and also target an antigen on a T-cell, e.g., CD3. In this way, the bispecific antibody targets both a cell of interest in a patient (e.g., B cell in a lymphoma patient, via CD20 binding) as well as a T-cell of the patient. The bispecific antibody, in various embodiments, is designed so as to activate the T-cell upon binding CD3, thus coupling T-cell activation to a specific, selected tumor cell.

Bispecific binding proteins that comprise two binding moieties that are each directed to a binding partner (i.e., each directed to a different target) on the surface of the same cell can also be made. This design is particularly suited to targeting specific cells or cell types that express both targets on the surface of the same cell. Although targets might appear individually on other cells, the binding moieties of these binding proteins are selected such that each binding moiety binds its target with a relatively low affinity (e.g., low micromolar, or high nanomolar—e.g., over a hundred nanomolar KD, e.g., 500, 600, 700, 800 nanomolar). In this way, prolonged target binding is favored only in situations where the two targets are in proximity on the same cell.

Bispecific binding proteins that comprise two binding moieties that bind the same target, each at a different epitope of the same target, can be made. This design is particularly suited for maximizing the probability of successfully blocking a target with binding protein. Multiple extracellular loops, e.g., of a transmembrane channel or a cell surface receptor, can be targeted by the same bispecific binding molecule.

Bispecific binding proteins that comprise two binding moieties that cluster and activate negative regulators of immune signaling to result in immune suppression can be made. Repression in cis can be achieved where the targets are on the same cell; repression in trans can be achieved where the targets are on different cells. Repression in cis, e.g., can be achieved with a bispecific binding protein having an anti-IgGRIIb binding moiety and an anti-FeID1 binding moiety, such that the IgGRIIb is clustered only in the presence of FeID1, in order to down-regulate an immune response to FeID1. Repression in trans, e.g., can be achieved with a bispecific binding protein having an anti-BTLA binding moiety and a binding moiety that specifically binds a tissue-specific antigen of interest, such that clustering of the inhibitory BTLA molecule occurs only in the selected target tissue, which potentially addresses auto-immune diseases.

Bispecific binding proteins that activate multi-component receptors can be made. In this design, two binding moieties directed to two components of a receptor bind, cross-link the receptor, and activate signaling from the receptor. This can be done, e.g., using a bispecific binding protein with a binding moiety that binds IFNAR1 and a binding moiety that binds IFNAR2, where binding cross-links the receptor. Such a bispecific binding protein can provide an alternative to interferon treatment.

Bispecific binding proteins that transport binding moieties across a semi-permeable barrier, e.g., the blood-brain barrier, can be made. In this design, one binding moiety binds a target that can transit a particular selective barrier; the other binding moiety targets a molecule with a therapeutic activity, wherein the target molecule with therapeutic activity cannot normally traverse the barrier. This kind of bispecific binding protein is useful for bringing therapeutics to tissues that the therapeutic would not otherwise reach. Some examples include targeting the pIGR receptor to transport a therapeutic into the gut or lung, or targeting the transferrin receptor to transport a therapeutic across the blood-brain barrier.

Bispecific binding proteins that transport binding moieties into specific cells or cell types can be made. In this design, one binding moiety targets a cell surface protein (e.g., a receptor) that is readily internalized into the cell. The other binding moiety targets an intracellular protein, where binding of the intracellular protein results in a therapeutic effect.

Bispecific binding proteins that bind a surface receptor of a phagocytic immune cell and a surface molecule of an infectious pathogen (e.g., a yeast or bacterium), to bring the infectious pathogen in the vicinity of a phagocytic immune cell to facilitate phagocytosis of the pathogen. An example of such a design would be a bispecific antibody that targets a CD64 or CD89 molecule and also a pathogen.

Bispecific binding proteins that have an antibody variable region as one binding moiety and a non-Ig moiety as a second binding moiety. The antibody variable region achieves targeting, whereas the non-Ig moiety is an effector or a toxin linked to an Fc. In this way, the ligand (e.g., an effector or toxin) is delivered to the target bound by the antibody variable region.

Bispecific binding proteins that have two moieties each bound to an Ig region (e.g., an Ig sequence containing a CH2 and CH3 region) such that any two protein moieties can be brought in each other's vicinity in the context of the Fc. Examples of this design include traps, e.g., homo- or heterodimeric trap molecules.

Nucleic Acids

Nucleic acid sequences encoding monoclonal antibodies can be obtained by any suitable method known in the art. Examples of suitable methods for obtaining monoclonal antibodies (and their nucleic acid sequences) include, for example, by a hybridoma method (see, e.g., Kohler et al. (1975) Nature 256:495-497) or a phage antibody library (see, e.g., see Clackson et al. (1991) Nature 352:624-628).

In various embodiments, the immunoglobulin heavy chain variable domains are derived from nucleic acid sequences of a genetically modified animal or a transgenic animal. In some embodiments, the regions are derived from an animal that comprises a human immunoglobulin minilocus. In some embodiments, the regions are derived from mice comprising one or more extrachromosomal nucleic acids that comprise one or more nucleic acids encoding immunoglobulin sequences. In various embodiments, the animal can have one or more unrearranged human immunoglobulin nucleic acid sequences. In some embodiments, the animal comprises human light chain variable regions nucleic acid sequences, in some embodiments human heavy chain variable sequences, in some embodiments both heavy and light chain variable sequences, and in some embodiments further comprises human constant region sequences. In a specific embodiment, the nucleic acid sequences are derived from a mouse in which endogenous mouse heavy chain variable gene segments and light chain variable gene segments have been replaced with human heavy chain variable gene segments and light chain variable gene segments.

In some embodiments, the nucleic acid sequences are derived from naive B or T cells of such an animal. In other embodiments, the nucleic acid sequences are derived from B or T cells of an animal that has been immunized with an antigen of interest.

In various embodiments, the nucleic acid sequences are derived from cells by amplifying them with primers, including for example sets of degenerate primers, that comprise one or more FR, joining, or constant sequences.

In various embodiments, the immunoglobulin heavy chain variable domains are derived from nucleic acids of an animal that has been immunized with an antigen of interest. For example, a non-human transgenic or genetically modified animal is immunized with the antigen of interest (by, e.g., exposing the animal to the antigen or a cell bearing the antigen or a nucleic acid encoding an expressible form of the antigen), allowing the animal to undergo an immune response, isolating immune cells (e.g., B cells) from the animal, optionally immortalizing the cells, and screening the cells to identify reactivity with the antigen and/or identifying and/or isolating a nucleic acid sequences that encode an immunoglobulin variable region that is capable of recognizing the antigen when placed in the context of an antibody. In some embodiments, the cell is a B cell. In some embodiments, a B cell of the immunized animal is used to make a hybridoma, and a B cell expressing an antibody that specifically recognizes an epitope of the antigen is identified and nucleic acid sequences that encode a variable region amino acid sequence that recognizes the epitope is identified and/or isolated.

In some embodiments, the nucleic acids are derived from humans, non-human primates (e.g., apes such as chimpanzees), monkeys (e.g., cynomologous or rhesus), rodents (e.g., mice, rats, hamsters), donkeys, goats, sheep, etc.

In some embodiments, the heavy chains comprise sequences that are derived from human cells. For example, human fetal cells exposed in vitro to an antigen and placed in a suitable host animal (e.g., a SCID mouse), In some embodiments, the nucleic acids are introduced into a cell using a vector. Vectors include, for example, plasmids, cosmids, retroviruses, adenoviruses, adeno-associated viruses, plant viruses, YACs, BACs, EBV-derived episomes.

In some embodiments, the nucleic acids are present in an expression vector or expression construct. In some embodiments, the expression vector or construct is a vector that contains a promoter operably linked to the nucleic acid sequence of interest such that the nucleic acid sequence of interest is capable of being expressed under suitable conditions in a suitable cell. Expression vectors or constructs can include leader sequences, enhancers, promoter elements that enhance transcription or translation, transcription stop sequences, splicing sequences, transcription-enhancing introns, IRES elements, marker genes, selection sequences, recombinase recognition sites, homology arms, viral sequences, operators (e.g., prokaryotic operators) etc. In some embodiments, the expression vectors comprise elements that allow inducible expression, for example, a prokaryotic operator operably linked to a eukaryotic promoter. In some embodiments, expression is induced upon addition of an expression inducer. In other embodiments, expression is induced upon removal of an expression inhibitor. In some embodiments, expression is induced by a temperature change.

In some embodiments, one or more heavy chain nucleotide sequences are on the same vector. In some embodiments, a heavy chain nucleic acid sequence and a light chain nucleic acid sequence herein are on the same vector. In one embodiment, two heavy chain nucleic acid sequences and a light chain nucleic acid sequence are on the same vector.

In some embodiments, the nucleic acids are expressed in a cell that comprises one or more nucleic acids from a virus. In specific embodiments, the virus is selected from adenovirus, adeno-associated virus, SV-40, Epstein-Barr virus, a retrovirus, a lentivirus, baculovirus, coronavirus, herpes simplex virus, poliovirus, Semliki Forest virus, Sindbis virus, and Vaccinia virus.

Host cells are cells that can be transformed to express a nucleic acid of interest. In various embodiments, transformation includes changing the nucleic acid content of a cell such that it contains exogenous nucleic acids (e.g., a nucleic acid not found in the cell in nature, or one or more additional copies of a nucleic acid corresponding to a nucleic acid sequence found in the cell in nature). The nucleic acid content of a cell can be changed by any suitable method known in the art, e.g., by integrating the nucleic acid into the cell's genome or by placing it in the cell in an extra-chromosomal or extra-genomic form. In some embodiments the nucleic acid content of the cell can be changed such that the cell transiently expresses the nucleic acid of interest, or the nucleic acid content can be changed such that the cell stably expresses the nucleic acid of interest. In some embodiments, the change in genetic content of the cell is inherited when the cell divides.

Isolating the Bispecific Antigen-Binding Protein

Once a suitable set of modifications were selected based on the information herein, attempts were made to isolate the bispecific antigen-binding protein using methods known in the art. Merely applying published method did not, in every circumstance, provide a satisfactory separation.

Lindhofer et al. made a bispecific antibody with a heterodimeric heavy chain having one heavy chain that bound Protein A (mouse IgG) and one heavy chain that did not (rat IgG), and successfully separated the rat/mouse heterodimeric bispecific antibody from a quadroma mixture of mouse/mouse and rat/rat dimers with a pH step gradient from neutral to pH 5.8 to elute the heterodimer and then a pH step from 5.8 to 3.5 to elute the mouse/mouse homodimer. (See Lindhofer et al. (1995) Preferential species-restricted heavy/light chain pairing in rat/mouse quadromas: Implications for a single-step purification of bispecific antibodies. J. Immunol. 155(1):219-225.)

The Lindhofer approach failed when applied to separating an IgG1 homodimer from an IgG1 heterodimer having two IgG1 heavy chains that were identical but for the fact that one of the IgG1 CH3 domains contained an H435R/Y436F dipeptide modification. The inventors found that in a linear pH gradient, the dipeptide-modified IgG1 eluted at about pH 3.9, whereas the IgG1 homodimer eluted at about pH 3.7. This pH difference was deemed insufficient to achieve a satisfactory separation of the heterodimer from the homodimer using the Lindhofer method. The difference was not reproducible in a predictable manner.

The variation in chromatographic behavior was observed in chromatographic runs that employed a relatively substantial ionic strength contributed by the buffer strength needed to maintain the particular pH step or gradient. But satisfactory separation was not achieved by adding an organic modifier (1-propanol). Instead, somewhat surprisingly, for some chromatographic runs the addition of 0.5 molar to 1.0 molar ionic modifier (e.g., NaCl) drastically and unexpectedly improved separation of homodimeric IgG1 and heterodimeric IgG1. Ionic modifier addition broadened the pH range for elution (1.2 pH units with ionic modifier, but 0.2 pH unit without ionic modifier) such that a pH step gradient could successfully separate the two species. In other runs, however, satisfactory separation was achieved with NaCl concentration of only about 150 mM (see Example 4). In order to ensure that satisfactory separation can be achieved, in one embodiment isolation of the bispecific antigen-binding protein is made in the presence of about 0.5 to about 1.0 molar ionic modifier.

Accordingly, in one embodiment a method for separating a bispecific antigen-binding protein comprising a heterodimeric IgG with one chain comprising a modification as described herein, comprises a step of employing a pH gradient in the presence of an ionic modifier. In one embodiment, the ionic modifier is present at a concentration sufficient to maximize the pH difference between elution from a Protein A support of an IgG homodimer and an IgG heterodimer as described herein (i.e., with CH3 modification(s)). In a specific embodiment, the ionic modifier is present at a concentration of about 0.5 to about 1.0 molar. In another specific embodiment, the ionic modifier is present at a concentration of about 0.15 to about 0.5 molar.

In one embodiment, the ionic modifier is a salt. In one embodiment, the ionic modifier is a salt of an alkaline metal or an alkaline earth metal and a halogen. In a specific embodiment, the salt is a chloride salt of an alkaline metal or an alkaline earth metal, e.g., NaCl, KCl, LiCl, $CaCl_2$, $MgCl_2$. In a specific embodiment, the salt is present at a molarity of about 0.5, 0.6, 0.7, 0.8, 0.9, or 1.0.

In one embodiment, the pH gradient is from about pH 3.9 to about pH 4.5, in another embodiment from about pH 4.0 to about pH 4.4, and in another embodiment about pH 4.1 to about pH 4.3. In a specific embodiment, the gradient is a linear gradient.

In one embodiment, the pH gradient is a step gradient. In one embodiment, the method comprises applying to an equilibrated Protein A column (equilibrated, e.g., in PBS or another suitable buffer or liquid) a step of about pH 3.9, about pH 4.0, about pH 4.1, about pH 4.2, about pH 4.3, or about pH 4.4. In a specific embodiment, the step is about pH 4.2.

In one embodiment, the bispecific antibody comprising the heterodimeric IgG CH3 domain elutes from the Protein A support in one or more fractions substantially free of non-heterodimeric IgG. In a specific embodiment, the eluted bispecific antibody fraction(s) comprise less than about 1%, 0.5%, or 0.1% of total protein by weight that is non-heterodimeric antibody.

EXAMPLES

The following examples are put forth so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Bispecific IL-4Ra/IL-6Ra Antigen-Binding Protein

It was found that two known antibodies of human IgG1 isotype, one against IL-4Ra and one against IL-6Ra, had light chains that differed by only four amino acids. Co-expression experiments revealed that the light chain of the anti-IL-4Ra antibody could be replaced with the light chain from the IL-6Ra and still maintain high affinity binding to IL-4Ra, thus making it feasible to produce a bispecific antibody using the anti-IL-4Ra heavy chain and the anti-IL-6Ra heavy chain and the same light chain. Accordingly, the heavy chain of the IL-6Ra antibody was modified to the FcΔAdp form (i.e., CH3 dipeptide modification H95R/Y96F, by IMGT exon numbering).

Figure 4:
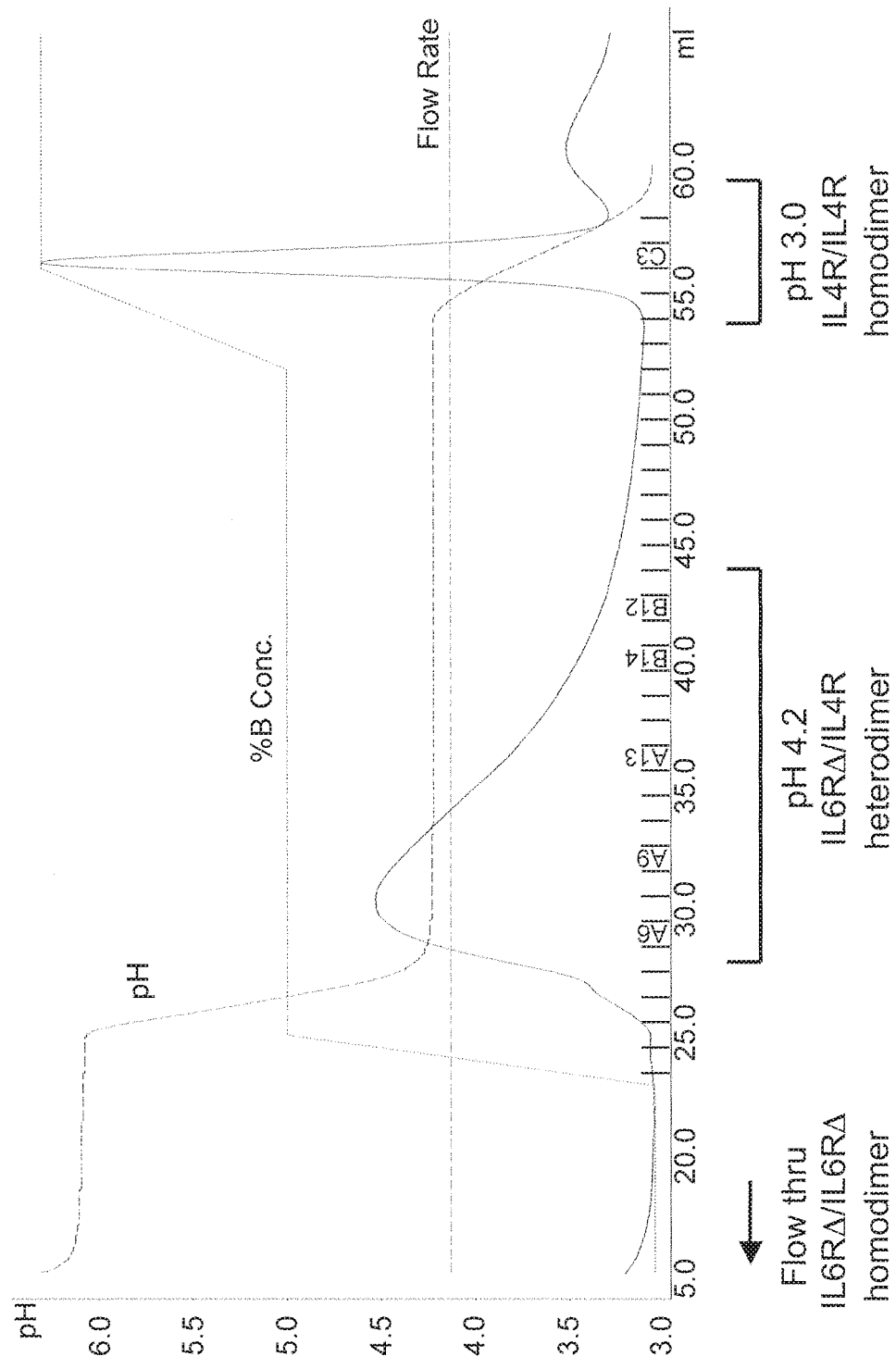
FIG. 4 shows a Protein A column trace for isolation of bispecific antibodies, showing an elution profile utilizing a step gradient.
Figure 5:
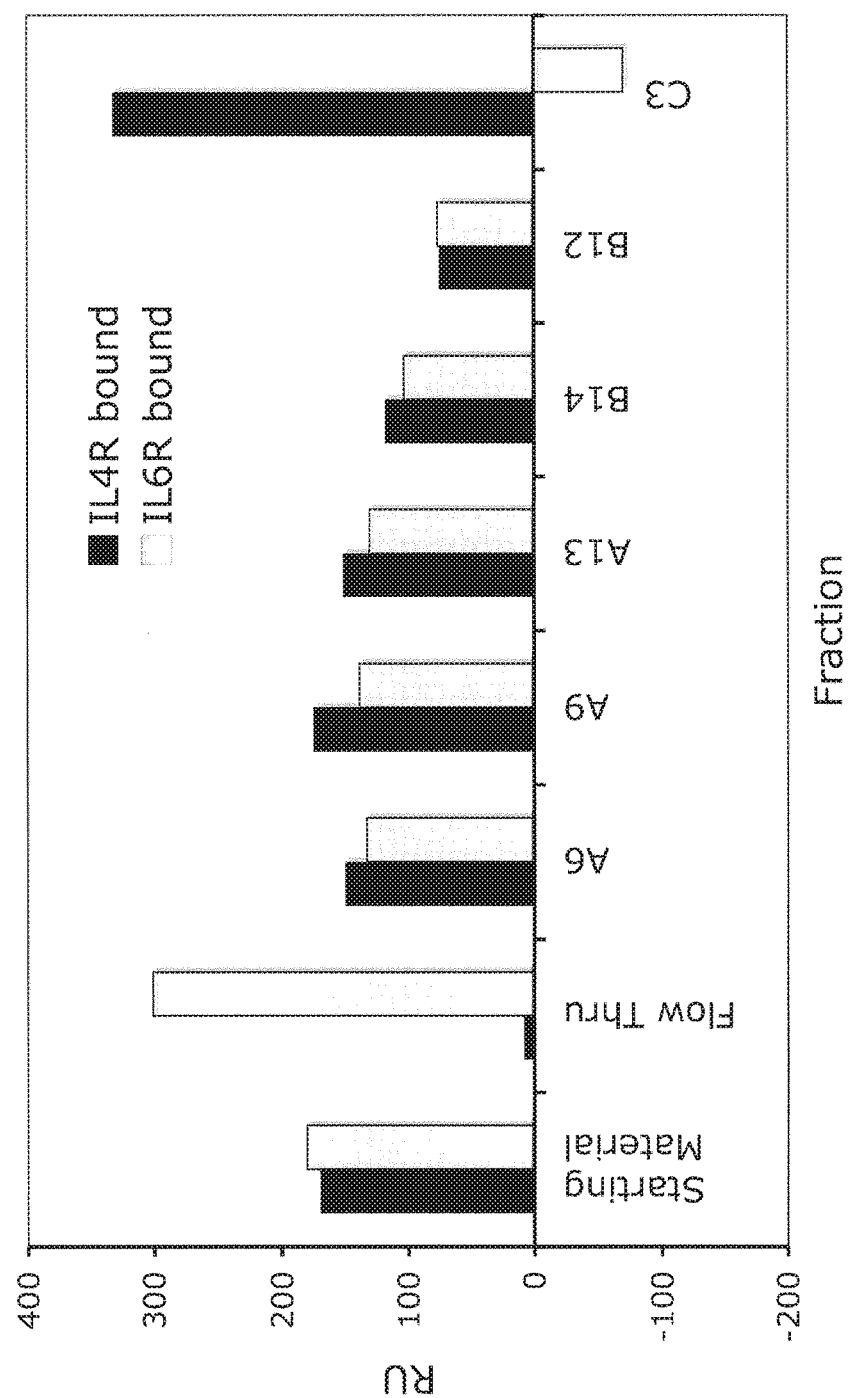
FIG. 5 shows IL4-Ra and IL-6Ra BIACORE™ binding profile of eluted column fractions from the chromatographic separation shown in FIG. 4. Antibodies in fractions were captured with immobilized anti-Fc antibodies, and then soluble IL-4Ra or IL-6Ra were assayed for binding to the captured antibodies.

The anti-IL-6Ra light chain was then co-expressed with the anti-IL4Ra/Fc and anti-IL6Ra/FcΔAdp heavy chains in CHO cells, and conditioned medium from these cells was subjected to Protein A chromatography. After loading the Protein A column with cell supernatants containing a mixture of homo- and heterodimers, the elution was performed with a pH step gradient produced by varying combinations of two buffers (A: 100 mM Na citrate, 150 mM NaCl, pH 6.0, and B: 100 mM Na citrate, 150 mM NaCl, pH 3.0; see FIG. 4) so as to produce three phases at pH 6.0, pH 4.2, and pH 3.0, respectively. In FIG. 4, IL-4R denotes anti-IL-4Ra, and IL-6RΔ denotes anti-IL-6Ra(IgG1ΔAdp). Indicated column fractions were assayed for binding to IL-6Ra and IL-4Ra proteins (see FIG. 5). A step elution was done, giving rise to one peak eluting at pH 4.2, and a second peak at pH 3.0 (FIG. 4). BIACORE™ analysis showed that the flow-through material could bind soluble IL-6Ra, but not IL-4Ra, as expected (FIG. 5). Fractions corresponding to the pH 4.2 peak could bind approximately equal amounts of IL-6Ra and IL-4Ra, consistent with the heterodimer. The peak eluting at pH 3.0 could bind only IL-4Ra, and not IL-6Ra, corresponding to the expected anti-IL-4Ra homodimer. This establishes that a heterodimeric bispecific antibody could be effectively isolated using Protein A chromatography, with a simple pH step gradient.

Example 2

Pharmacokinetics of FcΔAdp Proteins

Figure 6:
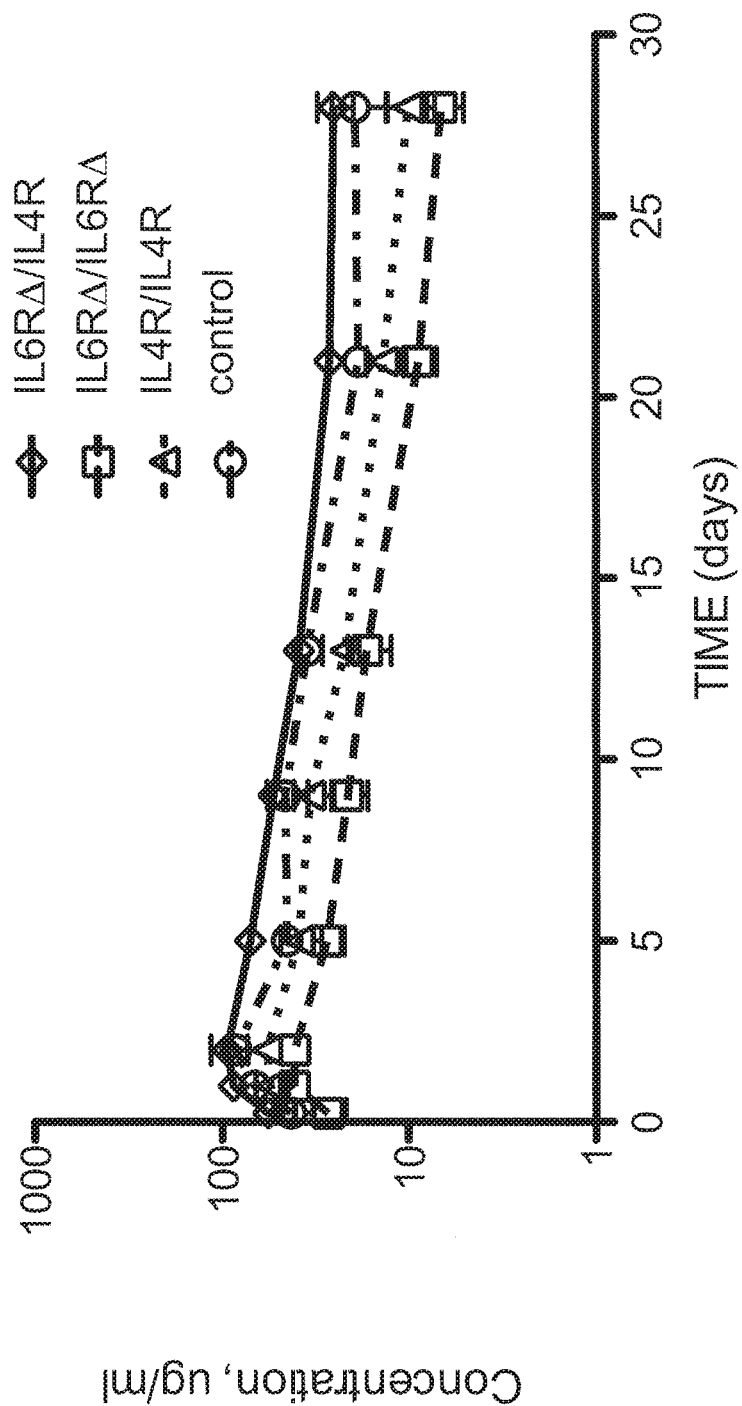
FIG. 6 shows a pharmacokinetic profile of an FcΔAdp bispecific antibody (IL-6RΔ/IL-4R), an FcΔAdp homodimer (IL-6RΔ/IL-6RΔ), an IgG1 antibody with wild-type CH3 sequence (IL-4R/IL-4R), and a control monospecific antibody.

To test whether the FcΔAdp modification affected the pharmacokinetics of a heterodimeric Fc/FcΔAdp containing molecule, mice were injected with the purified heterodimeric species of anti-IL-4Ra/anti-IL-6Ra described above, and concentrations of human immunoglobulin in serum were measured over a period of 28 days (FIG. 6; Table 1). The serum half-life of the heterodimer was about 10 days, similar to that of the wild type. This establishes that the FcΔAdp modifications had no detectable effect on serum half-life.

TABLE 1

| Drug | Pharmacokinetics (n = 5) Tested Half-life (Days) (avg. ± s.d.) |
|---|---|
| IL-6RΔ/IL-4R | 11.2 ± 1.8 |
| IL-6RΔ/IL-6RΔ | 10.8 ± 1.9 |
| IL-4R/IL-4R | 10.8 ± 1.9 |
| Control | 11.2 ± 1.9 |

Example 3

Bispecific CD20/CD3 Antigen-Binding Protein

Figure 7:
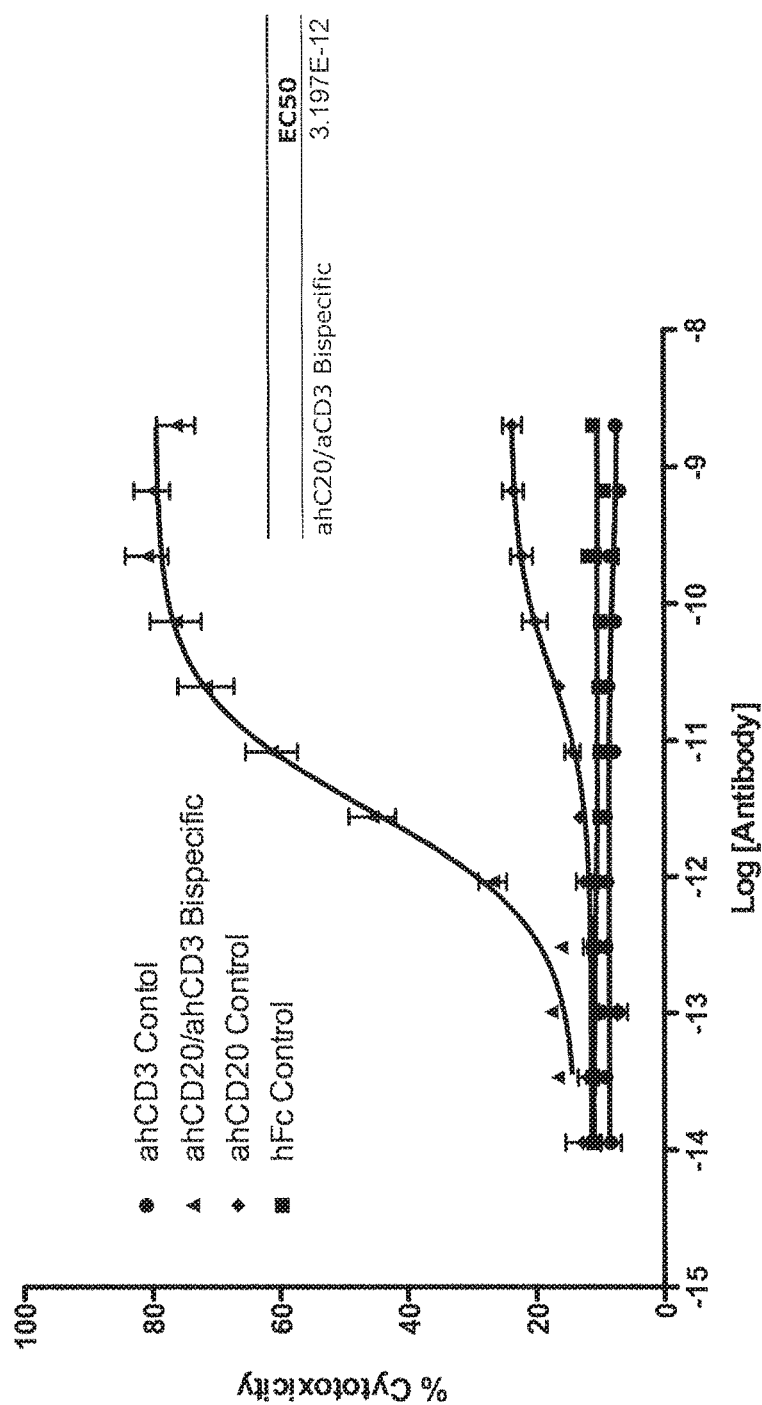
FIG. 7 illustrates efficacy of a CD20×CD3ΔAdp bispecific antibody in a Raji cell killing assay.

It was found that the heavy chain of a known anti-human CD20 antibody, when co-expressed with the light chain of a known (activating) anti-human CD3 antibody, was still able to bind CD20. The anti-CD3 light chain was then co-expressed with either the anti-CD20/Fc heavy chain, the anti-CD3/FcΔAdp heavy chain, or both heavy chains. The resulting mixed population of homo- and heterodimers was then used in a bioassay to determine ability to kill CD20 expressing target cells (FIG. 7). Briefly, $2 \times 10^7$ human PBMC cells were activated with $6 \times 10^7$ CD3×CD28 beads (Invitrogen) for 72 hours. Thirty units of IL-2 (R & D Systems) was then added and the cells were incubated for an additional 24 hours. The cells were then split to a concentration of $0.5 \times 10^6$/mL and an additional 30U IL-2 added. The cells were then incubated an additional 48 hours and used in the bioassay. On the day of the bioassay $2 \times 10^6$/mL CD20 expressing target cells (Raji) were labeled for 30 minutes with 8 uM calcein-AM (Invitrogen). Washed target cells were added to the activated hPBMC cells at a 1:10 ratio of target:effector cells (220,000 total cells per well) in 200 microliters total volume with the indicated amount of antibody containing supernatant. Cells were incubated for 2 hours and supernatant collected and fluorescence was quantified. Cytotoxicity was measured by calculating the ratio of the specific fluorescence to the maximal fluorescence. Neither the CD20 antibody alone (using the anti-CD3 light chain) nor the anti-CD3 antibody could provoke killing of the target cells; even mixing the two reagents had no effect. However, when all three components were co-expressed, significant killing was observed, indicating that the effect was due to the heterodimeric bispecific species. Based on the estimated amount of bispecific antibody in the transiently transfected CHO cell supernatant the $EC_{50}$ for this effect was estimated to be about 15 pM.

Example 4

Figure 8:
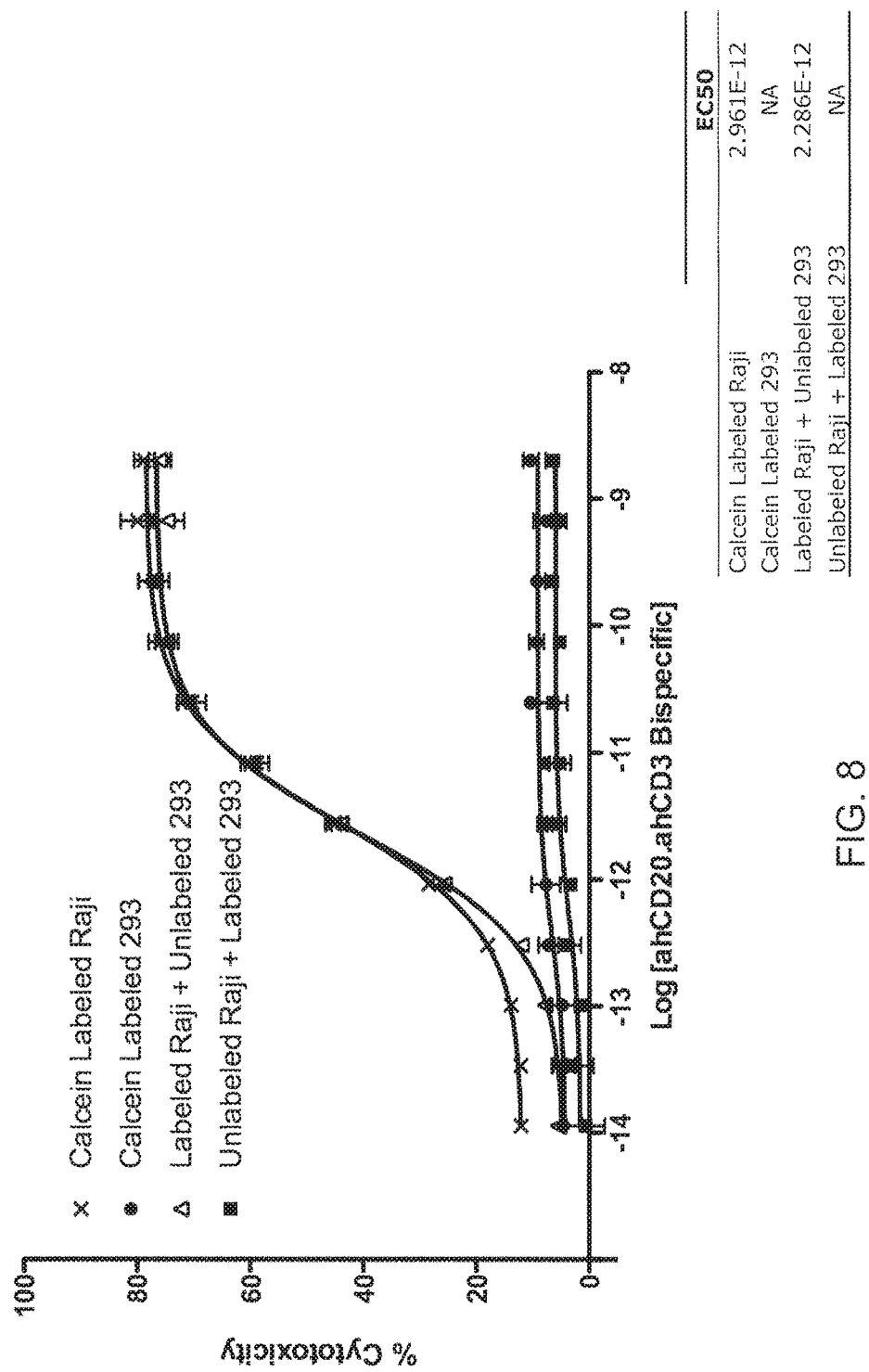
FIG. 8 illustrates a bystander cell (293) killing assay with the CD20×CD3ΔAdp bispecific antibody.

Cell Killing Specificity with Purified Bispecific CD20/CD3 Antigen-Binding Protein CHO cell supernatants from transfections as described in Example 3 were subjected to Protein A affinity chromatography, utilizing a step gradient for elution. The step gradient was produced by varying combinations of two buffers (A: 20 mM Na citrate, 1M NaCl, pH 5.2; B: 20 mM Na Citrate, 1M NaCl, pH 2.7) so as to produce three phases at pH 5.2, pH 4.2, and pH 2.8, respectively. Protein from the peak eluting at pH 4.2 was then used in a cell killing assay as described in Example 3. Target cell killing was observed at an $EC_{50}$ of 3 pM (FIG. 8). An additional cytotoxicity assay was performed which examined the target specificity of the observed killing. In this experiment labeled target cells expressing CD20 (Raji) or without CD20 (293) were incubated with activated human PBMCs. Each target cell type was added to the assay either alone or in combination with unlabeled target cells of the other type. In all cases the CD20 expressing target cells were killed specifically with an $EC_{50}$ of 3 pM while the CD20 negative cell line was not killed.

Example 5

Protein A Separation of a Differentially Modified hIgG2 Fc

Differentially modified heterodimeric human IgG2 Fc/ΔAdpFc and an unmodified human homodimeric IgG2 Fc/Fc were first enriched by a bind-and-wash process through a protein A column (rProtein A FF, GE). To further separate hIgG2 Fc/ΔAdpFc from hIgG2 Fc/Fc, a step-gradient elution was performed using a SMART™ system (GE) as follows. The solvent system consisted of solvent A (PBS, 1×), solvent B (20 mM sodium citrate and 1 M NaCl, pH 5.5) and solvent C (20 mM sodium citrate and 1M NaCl, pH 2.5). The elution started with an isocratic elution with 100% A in the first 20 min followed by a quick switch to 100% B at 20 min. A linear gradient to 33.5% C and 66.5% B was then initiated over the next 10 min; the concentration of 33.5% of C was maintained for 20 min until the complete elution of the first peak (Fc/ΔAdpFc). A linear gradient from 33.5% C to 100% C was followed for 30 min. The flow rate was kept 250 microliters/min and the chromatograms were detected at 280 nm by a UV detector. The hIgG2 Fc/ΔAdpFc eluted at pH 4.5, whereas the hIgG2 eluted at pH 3.5.

Example 6

Protein A Separation of a Differentially Modified hIgG4 Fc

Differentially modified heterodimeric human IgG4 (Fc/ΔAdpFc) and an unmodified homodimeric IgG4 (Fc/Fc) were first enriched by a bind-and-wash process through a protein A column (rProtein A FF, GE). To further separate hIgG4 Fc/ΔAdpFc from hIgG4 Fc/Fc, a step-gradient elution was performed using a SMART™ system (GE) as follows. The solvent system consisted of solvent A (PBS, 1×), solvent B (20 mM sodium citrate and 1 M NaCl, pH 5.1) and solvent C (20 mM sodium citrate and 1M NaCl, pH 2.8). The elution started with an isocratic elution with 100% A in the first 20 min followed by a quick switch to 100% B at 20 min. A linear gradient to 50% C and 50% B was then initiated over the next 10 min; the concentration of 50% of C was maintained for 20 min until the complete elution of the first peak (Fc/ΔAdpFc). A linear gradient from 50% C to 100% C was followed for 30 min. The flow rate was kept 250 microliters/min and the chromatograms were detected at 280 nm by a UV detector. The hIgG4 Fc/AdpFc eluted at about pH 4 whereas the homodimer eluted during a gradient from about pH 4 to pH 2.8.

Example 7

Protein A Separation of a Differentially Modified hIgG1 CD3×CD20

Differentially modified heterodimeric anti-hCD3×CD20 IgG1 (Fc/ΔAdpFc) and an unmodified homodimeric antihCD20 were separated on a 1 mL rProtein AFF (GE Biosciences) column as follows. The solvent system was buffer A1 (PBS 1×), buffer A2 (20 mM sodium citrate and 1 M NaCl pH 5.1), buffer B (20 mM sodium citrate and 1 M NaCl pH 2.8). The mixed sample was bound and washed in PBS and buffer A2. A step was used to attain a pH of 4.2, which eluted bispecific CD3*×CD20 IgG1 (Fc/ΔAdpFc), then a linear gradient from pH 4.2 to pH 2.8 eluted the homodimeric anti-hCD20 IgG1.

Example 8

Binding Affinity of Modified CH3s to Fc Receptors

The binding affinity of a human IgG1 isotype bispecific antibody having the ΔAdp modification (H435R and Y436F, EU numbering) to a variety of human Fc receptors was tested in a Biacore™ steady state equilibrium binding assay.

Briefly, a carboxymethylated dextran (CM5) chip having an amine-coupled anti-penta-his mAb (Qiagen) was used to capture various constructs of human Fc receptors. The following his-tagged Fc receptor ectodomains were bound to the surfaces of different anti-penta-his-coated CM5 chips: FcγRI, FcγRIIA(R131 polymorph), FcγRIIB, and FcγRIIIB (each obtained from R&D Systems); and RcγRIIA(H131 polymorph), FcγRIIIA(V176 polymorph), and RcγRIIIA (F176 polymorph) (each made at Regeneron). Antibodies were passed over the surface at three concentrations for the high affinity receptor FcγR1 ectodomain (25 nM, 50 nM, and 100 nM), and at between 5 micromolar to 39 nanomolar for the low affinity FcγR receptor ectodomains, and association and dissociation rate constants ($k_a$ and $k_d$) values were determined and used to calculate equilibrium dissociation constants ($K_D$s) for the antibodies. Binding studies were performed at room temperature using HBS-T buffer at pH 7.2 $K_D$s were determined for a control antibody (hmAb), an anti-CD20, and anti-CD3Δdp modification, and a CD20×CD3Adp bispecific antibody. $K_D$ values for the anti-CD3Δdp antibody revealed no significant differences in binding to any of the Fc receptors tested as compared with unmodified hIgG1 isotype antibodies (Table 2).

TABLE 2

$K_D$ (nM) for Binding of hIgG Abs to hFcγR Ectodomains

| | Human IgG1 Homodimer | | Human IgG1 ΔAdp | |
|---|---|---|---|---|
| hFcR | hmAb | CD20-hFc | CD3-hFc ΔAdp Homodimer | Bispecific CD20×CD3 ΔAdp Heterodimer |
| FcγR1 | 5.00 | 4.27 | 3.17 | 3.61 |
| FcγRIIA(R131) | 1,460 | 739 | 588 | 328 |
| FcγRIIA(H131) | 915 | 458 | 451 | 222 |
| FcγRIIB | 3,400 | 1,850 | 1,360 | 794 |
| FcγRIIIA(V176) | 810 | 430 | 218 | 248 |
| FcγRIIIA(F176) | 2,500 | 533 | 407 | 267 |
| FcγRIIIB | 3,700 | 1,170 | 906 | 520 |

Example 9

Pharmacokinetics of a Bispecific hIgG1ΔAdp in hFcRn Mice

The pharmacokinetic clearance rate of bispecific anti-hCD3/hCD20 IgG1ΔAdp antibody and its antibody related controls (anti-hCD3 IgG and anti-hCD3 IgGΔAdp homodimer) were determined in wild-type (WT) mice and mice homozygous for a replacement of mouse FcRn with a hFcRn gene (hFcRn mice). Wild-type and hFcRn mice were from cross-bred strains with a background containing C57BL6 (75%) and 129Sv (25%). Cohorts contained 4 each of either WT or hFcRn mice, except in the case of one cohort of WT mice receiving an IgG1 isotyped matched control antibody in which the cohort contained 3 mice. Mice received 1 mg/kg of an isotype-matched (hIgG1) control, anti-hCD3×CD20 IgG1ΔAdp bispecific, anti-hCD3 IgG1, or anti-hCD3 IgG1ΔAdp homodimer. All test articles were administered subcutaneously. Bleeds were collected at 0 h, 6 h, 1d, 2d, 3d, 4d, 7d, 10d, 14d, 21d, and 30d.

Serum levels of human antibodies were determined by a sandwich ELISA. Briefly, a goat polyclonal anti-human IgG (Fc-specific) antibody (Jackson ImmunoResearch) was coated in 96-well plates at a concentration of one microgram/mL and incubated overnight at 4° C. After the plates were blocked with BSA, serum samples in six-dose serial dilutions and reference standards of the respective antibodies in 12-dose serial dilutions were added to the plate and incubated for one hour at room temperature. After washing to remove unbound antibody, captured human antibodies were detected using the same goat polyclonal anti-human IgG (Fc-specific) antibody conjugated with horseradish peroxidase (HRP) (Jackson ImmunoResearch) and developed by standard colorimetric tetramethylbenzidine (TMB) substrate according to manufacturer's recommendation. Absorbance at 450 nm were recorded on a plate reader and the concentration of hIgG in serum samples were calculated using the reference standard curve generated in the sample plate.

No significant difference was observed in the serum half-life of the four IgG1 antibodies over the 30-day period tested. In particular, there was no significant difference observed between IgG1 antibodies having the ΔAdp modification and wild-type IgG1 antibodies. No difference among the antibodies was observed with either wild-type (mFcRn) mice or mice having a humanized FcRn (hFcRn). As expected, hFcRn mice exhibited a slightly faster clearance than wild-type mice. Results are shown in Table 3.

TABLE 3

Mean PK Parameter Estimates after Subcutaneous Injection in Mice

| Mouse Genotype | Antibody | n | $C_{max}$ (mcg/mL) | AUC ((hr)(mcg/mL)) |
|---|---|---|---|---|
| mFcRn | CD3×CD20 | 4 | 9.0 ± 2.3 | 114.3 ± 30.6 |
| | CD3 | 4 | 11.1 ± 1.7 | 175.4 ± 56.4 |
| | CD3ΔAdpΔAdp | 4 | 11.7 ± 1.8 | 155.3 ± 34.02 |
| | Control hIgG | 3 | 15.1 ± 3.01 | 162.5 ± 27.02 |
| hFcRn | CD3×CD20 | 4 | 12.3 ± 0.98 | 83.2 ± 18.6 |
| | CD3 | 4 | 7.7 ± 2.2 | 65.2 ± 16.5 |
| | CD3ΔAdpΔAdp | 4 | 9.9 ± 1.34 | 70.4 ± 15.4 |
| | Control hIgG | 4 | 16.1 ± 2.7 | 131.3 ± 20.4 |

Example 10

Large-Scale Isolation in Low-Salt Buffer

A bispecific CD3×CD20ΔAdp antibody was isolated according to the invention from a large-scale culture. Briefly, a CHO-K1 cell line expressing a bispecific anti-hCD3×CD20ΔAdp (modification on the CD3 heavy chain) antibody were cultured in an 11-liter bioreactor. Cells bearing the bispecific antibody grew to a density of about 8.25×10⁶ cells/mL, yielding about 250-350 mg antibody/L. In contrast, a control anti-hCD3 antibody yielded about 100-150 mg/L.

Antibody was isolated on an MabSelect SuRe™ resin (GE) (20 cm bed height, 1 cm ID) equilibrated with 10 mM sodium phosphate, 0.5 M NaCl, pH 7.2, clarified cell culture loaded to 19 g/L, and the column was washed with 3 column volumes of 10 mM sodium phosphate, 0.5 M NaCl, pH 7.2, followed by a wash of 2 column volumes of 20 mM sodium phosphate, pH 7.2 (no NaCl). Antibody was eluted with 40 mM acetate, pH 3.0.

The monospecific anti-CD30 antibody eluted at pH 3.6, whereas the bispecific anti-hCD3×CD20DAdp eluted at pH 4.4

Example 11

Selective Protein A Elution of Mouse Heterodimers with Mild pH

CHO-K1 cells were transiently transfected with expression constructs for human IFNAR1 (hIFNAR1) and human IFNAR2 (hIFNAR2) extracellular domain fused with a wild type or a mutant (TTTK or PTTK) mIgG2a Fc. The ratio between hIFNAR1-mFc and hIFNAR2-mFc was held at 1:1 by transfecting cells with equal amounts of the two expression plasmids. Culture medium was collected 4 days after transfection and subjected to Protein A purification using 0.2 mL NAb Protein A Plus™ spin columns (Thermo Scientific/Pierce). Briefly, the columns were equilibrated with 1×PBS, pH 7.2. One ml of CHO-K1 culture medium was incubated with the Protein A resin for 10 minutes at room temperature. The columns were then washed three times with 1×PBS, pH 7.2. Bound proteins were eluted with 20 mM sodium citrate buffer containing 1M NaCl. Three elutions were carried out using 0.4 mL of elution buffer with decreasing pH. Proteins in the different fractions were detected by Western blot analysis.

The results show that with pH gradient elution, it is possible to separate heterodimers of wild type and star mutant mIgG2a from homodimers of wild type mIgG2a (see fraction E1 on both gels of FIG. 9).

Example 12

Preferential Heterodimer Formation of mIgG2a Mutants Over Isotype Heterodimers

DNA plasmids were constructed for mammalian expression of the extracellular domains of human type I interferon receptors (hIFNAR1 and hIFNAR2) with C-terminal mouse Fc (mIgG2a or mIgG1). Mutations in the mIgG2a sequence were introduced using site-directed mutagenesis. The mutants are TTT=M252T, S254T, S256T; TTTK=M252T, S254T, S256T, I258K; PTTTK=I247P, M252T, S254T, S256T, I258K; RF=H435R, H436F. CHO-K1 cells were transiently transfected with the expression constructs. The ratio between IFNAR1-mFc and IFNAR2-mFc was held at 4:1 by transfecting cells with 4-fold more hIFNAR1-mFc expression plasmid (hIFNAR1-mIgG2a) than hIFNAR2-mFc (mIgG1 or mutant mIgG2a). Culture medium was collected 4 days after transfection and mFc proteins were detected by Western blot analysis.

Figure 10:
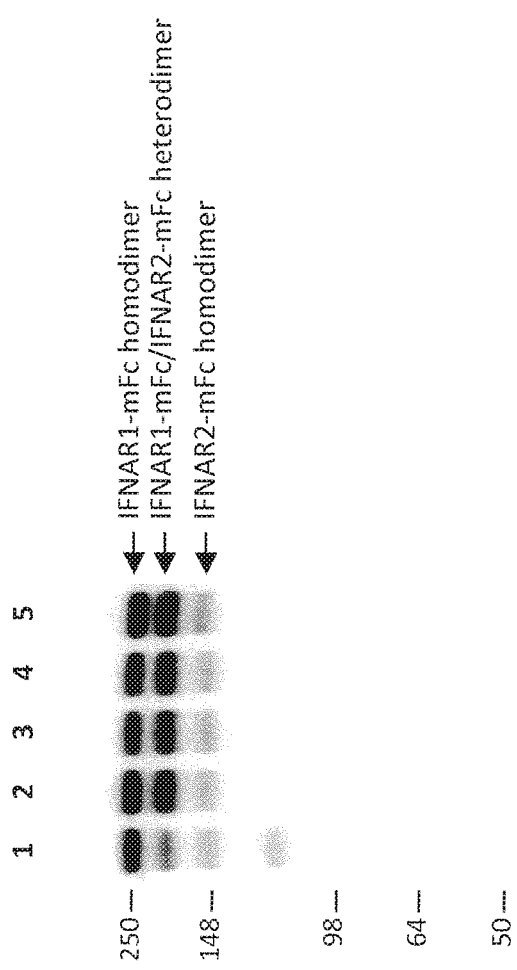
FIG. 10 illustrates preferential formation of heterodimers of mutant IgG2a over formation of heterodimers of mixed isotypes (e.g., mIgG2a and m IgG1), using IFNAR1 construct:IFNAR2 construct ratio of 4:1. Lane 1: IFNAR1-IgG2a:IFNAR2-IgG1; Lane 2: INFAR1-IgG2a:IFNAR2-IgG2aTTT; Lane 3: IFNAR1-IgG2a:IFNAR2-IgG2aTTTK; Lane 4: IFNAR1-IgG2a:IFNAR2-IgG2aPTTTK; Lane 5: IFNAR1-IgG2a:IFNAR2-IgG2aRF.

The result shows that heterodimer formation between mIgG2a and mIgG1 is much less efficient than that between wild type mIgG2a and mIgG2a mutants (compare lane 1 to lanes 2 to 5 of FIG. 10). A ratio of 4:1 IFNAR1 construct: IFNAR2 construct was used to maintain an excess of wild-type IgG2a construct in the experiment.

What is claimed is:

1. A method for isolating a bispecific antigen-binding protein, comprising:
   contacting a disrupted cell or a mixture of antigen-binding proteins with a Protein A affinity support; and
   eluting a bispecific antigen-binding protein with a pH gradient, in the presence of an ionic modifier;
   wherein the bispecific antigen-binding protein comprises a heterodimeric IgG CH3 region comprising a first and a second IgG CH3 domain, each with a different affinity to Protein A.

2. The method of claim 1, wherein the ionic modifier is a salt selected from the group consisting of beryllium acetate, lithium acetate, sodium acetate, potassium acetate, sodium bicarbonate, potassium bicarbonate, lithium carbonate, sodium carbonate, potassium carbonate, cesium carbonate, lithium chloride, sodium chloride, potassium chloride, cesium chloride, magnesium chloride, sodium fluoride, potassium fluoride, sodium nitrate, potassium nitrate, calcium nitrate, sodium phosphate, potassium phosphate, calcium sulfate, magnesium sulfate, an alkaline metal salt, an alkaline earth metal salt, and a halogen salt.

3. The method of claim 1, wherein the ionic modifier is present at a concentration of about 0.15 to about 0.5 molar.

4. The method of claim 3, wherein the ionic modifier is NaCl and it is present at a concentration of at least about 150 mM.

5. The method of claim 1, wherein the ionic modifier is present at a concentration of about 0.5 to about 1.0 molar.

6. The method of claim 1, wherein the pH gradient comprises a gradient from about pH 4.0 to about pH 4.4.

7. The method of claim 1, wherein the pH gradient is a linear gradient.

8. The method of claim 1, wherein the pH gradient is a step gradient.

9. The method of claim 1, wherein the bispecific antigen-binding protein elutes at a pH between about 3.9 to about 4.4.

10. The method of claim 8, wherein the bispecific antigen-binding protein elutes at a pH of about 4.2.

11. The method of claim 1, wherein the mixture is culture medium.

12. The method of claim 1, wherein the bispecific antigen-binding protein comprising the heterodimeric IgG CH3 region elutes in one or more fractions comprising less than about 1% of total protein by weight antibodies comprising a homodimeric IgG CH3 region that comprises CH3 domains with the same affinities with respect to Protein A.

13. The method of claim 1, wherein the second IgG CH3 region comprises a modification that reduces or eliminates binding of the second CH3 region to Protein A.

14. The method of claim 13, wherein the first and second IgG CH3 domains are each a human IgG heavy chain CH3 domain selected from the group consisting of a human IgG1 heavy chain CH3 domain, a human IgG2 heavy chain CH3 domain, and a human IgG4 heavy chain CH3 domain.

15. The method of claim 14, wherein the modification is selected from the group consisting of (a) 95R, and (b) 95R and 96F in the IMGT exon numbering system, or (a') 435R, and (b') 435R and 436F in the EU numbering system.

16. The method of claim 15, wherein the second IgG CH3 domain is
   a human IgG1 CH3 domain and further comprises one to five modifications selected from the group consisting of 16E, 18M, 44S, 52N, 57M, and 82I in the IMGT exon numbering system, or 356E, 358M, 384S, 392N, 397M, and 422I in the EU numbering system,
   a human IgG2 CH3 domain and further comprising one or two modifications selected from the group consisting of 44S, 52N, 82I in the IMGT exon numbering system, or 348S, 392N and 422I in the EU numbering system, or
   a human IgG4 CH3 domain and further comprising one to seven modifications selected from the group consisting of 15R, 44S, 52N, 57M, 69K, 79Q and 82I in the IMGT exon numbering system or 355R, 384S, 392N, 397M, 409K, 419Q and 422I in the EU numbering system.

17. The method of claim 15, wherein the second IgG CH3 domain is a human IgG4 CH3 domain and further comprises the modification 105P in the IGMT exon numbering system or 445P in the EU numbering system.

18. The method of claim 1, wherein the first and second IgG CH3 domains are the same isotype.

19. The method of claim 1, wherein the heterodimeric CH3 regions of the bispecific antigen-binding protein is non-immunogenic or substantially non-immunogenic in a human.

20. The method of claim 1, wherein the bispecific antigen-binding protein comprises two light chains that are the same.

21. The method of claim 1, wherein the bispecific antigen-binding protein displays a pharmocokinetic profile equivalent to the same bispecific antigen-binding protein having a homodimeric IgG CH3 region.

22. The method of claim 1, wherein the Protein A affinity support is a Protein A column.

* * * * *

UNITED STATES PATENT AND TRADEMARK OFFICE
CERTIFICATE OF CORRECTION

| | |
|---|---|
| PATENT NO. | : 9,982,013 B2 |
| APPLICATION NO. | : 15/058026 |
| DATED | : May 29, 2018 |
| INVENTOR(S) | : Samuel Davis et al. |

It is certified that error appears in the above-identified patent and that said Letters Patent is hereby corrected as shown below:

On the Title Page

Item (74) Attorney, Agent, or Firm:
"FisherBroylers, LLP" should read --FisherBroyles, LLP--

On Page 2
Item (56) OTHER PUBLICATIONS:
Line 4 "of Immunoglogi-" should read --Journal of Immunologi- --

In the Drawings

Sheet 8 of 11:
Figure 7
"Contol" should read --Control--

In the Specification

Column 3, Line 30:
"IL4-Ra" should read --IL-4Ra--

Column 6, Line 52:
"PERC.6TM" should read --PER.C6TM--

Column 7, Line 7:
"PIPS" should read --PIP3--

Column 21, Line 52:
"mouse)," should read --mouse).--

Signed and Sealed this
Fourth Day of December, 2018

Andrei Iancu
*Director of the United States Patent and Trademark Office*

CERTIFICATE OF CORRECTION (continued)
U.S. Pat. No. 9,982,013 B2

Column 27, Line 38:
"CD3Adp" should read --CD3ΔAdp--

Column 29, Line 14:
"anti-hCD3xCD20DAdp" should read --anti-hCD3xCD20ΔAdp--

Column 29, Line 15:
"4.4" should read --4.4.--

SEQUENCE LISTING

<160> NUMBER OF SEQ ID NOS: 7

<210> SEQ ID NO 1
<211> LENGTH: 107
<212> TYPE: PRT
<213> ORGANISM: Homo sapiens

<400> SEQUENCE: 1

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 2
<211> LENGTH: 107

```
<212> TYPE: PRT
<213> ORGANISM: Homo sapiens

<400> SEQUENCE: 2

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 3
<211> LENGTH: 107
<212> TYPE: PRT
<213> ORGANISM: Homo sapiens

<400> SEQUENCE: 3

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 4
<211> LENGTH: 107
<212> TYPE: PRT
<213> ORGANISM: Homo sapiens

<400> SEQUENCE: 4

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn Arg Phe
```

Thr Gln Lys Ser Leu Ser Leu Ser Pro Gly Lys
            100                 105

<210> SEQ ID NO 5
<211> LENGTH: 107
<212> TYPE: PRT
<213> ORGANISM: Homo sapiens

<400> SEQUENCE: 5

Gly Gln Pro Arg Glu Pro Gln Val Tyr Thr Leu Pro Pro Ser Gln Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 6
<211> LENGTH: 107
<212> TYPE: PRT
<213> ORGANISM: Homo sapiens

<400> SEQUENCE: 6

Gly Gln Pro Arg Glu Pro Gln Val Tyr Thr Leu Pro Pro Ser Gln Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Leu Gly Lys
            100                 105

<210> SEQ ID NO 7
<211> LENGTH: 107
<212> TYPE: PRT
<213> ORGANISM: Homo sapiens

<400> SEQUENCE: 7

Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

```
Asn Asn Tyr Asn Thr Thr Pro Pro Met Leu Asp Ser Asp Gly Ser Phe
     50              55                  60

Phe Leu Tyr Ser Lys Leu Thr Val Asp Lys Ser Arg Trp Gln Gln Gly
65               70              75                      80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100             105
```